(12) United States Patent
Jannard

(10) Patent No.: US 8,876,285 B2
(45) Date of Patent: *Nov. 4, 2014

(54) WEARABLE HIGH RESOLUTION AUDIO VISUAL INTERFACE

(71) Applicant: Oakley, Inc., Foothill Ranch, CA (US)

(72) Inventor: James H. Jannard, Eastsound, WA (US)

(73) Assignee: Oakley, Inc., Foothill Ranch, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/046,165

(22) Filed: Oct. 4, 2013

(65) Prior Publication Data

US 2014/0098424 A1    Apr. 10, 2014

Related U.S. Application Data

(63) Continuation of application No. 13/651,999, filed on Oct. 15, 2012, now Pat. No. 8,550,621, which is a
(Continued)

(51) Int. Cl.
| | | |
|---|---|---|
| *G02C 1/00* | (2006.01) | |
| *A61B 5/00* | (2006.01) | |
| *G02B 27/01* | (2006.01) | |
| *A61B 5/11* | (2006.01) | |
| *A61B 5/145* | (2006.01) | |
| *A61B 5/024* | (2006.01) | |
| *A61B 5/021* | (2006.01) | |

(52) U.S. Cl.
CPC ......... *G02B 27/0179* (2013.01); *A61B 5/14532* (2013.01); *A61B 5/6814* (2013.01); *G02B 27/0176* (2013.01); *A61B 5/1112* (2013.01); *G02B 2027/0156* (2013.01); *A61B 5/145* (2013.01); *A61B 5/6803* (2013.01); *A61B 5/02438* (2013.01); *A61B 5/021* (2013.01)
USPC ....................................... 351/158

(58) Field of Classification Search
CPC .................... G02B 27/017; G02B 2027/0178; G02B 27/0093; G02B 2027/0118; G02B 2027/0127; G02B 2027/0123; G02B 27/01; G02C 11/04
USPC ......... 351/158, 41; 345/7, 8, 9; 381/364, 370, 381/381
See application file for complete search history.

(56) References Cited

U.S. PATENT DOCUMENTS

| 1,026,272 A | 5/1912 | Leveque |
| 1,370,806 A | 3/1921 | Garner |

(Continued)

FOREIGN PATENT DOCUMENTS

| CH | 660531 | 4/1987 |
| CN | 2108942 | 7/1992 |

(Continued)

OTHER PUBLICATIONS

Ajluni, Cheryl. "Wearable Wireless Redefines Computer Usage", Wireless Systems Design, pp. 14-16, Dec. 2002.

(Continued)

*Primary Examiner* — Hung Dang
(74) *Attorney, Agent, or Firm* — Knobbe Martens Olson & Bear, LLP

(57) ABSTRACT

An adjustable visual optical element is provided, which may be supported, for example, by an eyeglass. The optical element is preferably adjustable in each of the X, Y, and Z axes to allow the wearer to optimize projection of the optical element. A view axis of the display is preferably also angularly adjustable with respect to a wearer's straight ahead normal line of sight. Source electronics may be carried onboard the eyeglasses, or may be connectable to the eyeglasses via either a hardwire, optical guide, or radiofrequency link.

18 Claims, 12 Drawing Sheets

Related U.S. Application Data continuation of application No. 13/245,461, filed on Sep. 26, 2011, now Pat. No. 8,313,192, which is a continuation of application No. 12/820,099, filed on Jun. 21, 2010, now Pat. No. 8,025,398, which is a continuation of application No. 11/955,249, filed on Dec. 12, 2007, now Pat. No. 7,740,353.

(60) Provisional application No. 60/870,064, filed on Dec. 14, 2006.

(56) References Cited

U.S. PATENT DOCUMENTS

| | | | |
|---|---|---|---|
| D130,310 | S | 11/1941 | Monjar |
| 2,424,935 | A | 7/1947 | Kimmel |
| 2,504,524 | A | 4/1950 | Hayward |
| 2,688,900 | A | 9/1954 | Silverman |
| 2,856,466 | A | 10/1958 | Gustafson et al. |
| 2,882,348 | A | 4/1959 | Erickson |
| 2,915,598 | A | 12/1959 | Brunton |
| 2,947,822 | A | 8/1960 | Matsuura |
| 2,999,136 | A | 9/1961 | Holt et al. |
| 3,104,290 | A | 9/1963 | Rosemond et al. |
| 3,119,903 | A | 1/1964 | Rosemond et al. |
| D201,050 | S | 5/1965 | Gieseking et al. |
| 3,247,330 | A | 4/1966 | Hinman |
| D207,919 | S | 6/1967 | Lui Fai |
| 3,327,836 | A | 6/1967 | Burt |
| 3,371,979 | A | 3/1968 | Catanzaro |
| D212,863 | S | 12/1968 | Roberts |
| 3,495,898 | A | 2/1970 | Del Vecchio |
| 3,536,385 | A | 10/1970 | Johnston |
| 3,588,384 | A | 6/1971 | Negley |
| 3,665,122 | A | 5/1972 | Weiss |
| D228,677 | S | 10/1973 | Wichers |
| 3,769,663 | A | 11/1973 | Perl |
| D229,974 | S | 1/1974 | Wichers et al. |
| 3,809,829 | A | 5/1974 | Vignini et al. |
| 3,853,393 | A | 12/1974 | Fila et al. |
| 3,883,701 | A | 5/1975 | Delorenzo |
| 3,943,925 | A | 3/1976 | Leight |
| 3,957,184 | A | 5/1976 | Shurman |
| 4,006,974 | A | 2/1977 | Resnick |
| 4,149,780 | A | 4/1979 | Young |
| 4,283,127 | A | 8/1981 | Rosenwinkel et al. |
| 4,294,792 | A | 10/1981 | Arons et al. |
| 4,537,612 | A | 8/1985 | Borrelli et al. |
| 4,550,984 | A | 11/1985 | Reymond |
| 4,600,077 | A | 7/1986 | Drever |
| 4,636,048 | A | 1/1987 | Jones |
| 4,683,587 | A | 7/1987 | Silverman |
| D292,986 | S | 12/1987 | Magestro |
| 4,712,244 | A | 12/1987 | Zwicker |
| 4,773,095 | A | 9/1988 | Zwicker |
| 4,803,487 | A | 2/1989 | Willard et al. |
| 4,806,011 | A | 2/1989 | Bettinger |
| 4,856,086 | A | 8/1989 | McCullough |
| 4,869,575 | A | 9/1989 | Kubik |
| 4,882,769 | A | 11/1989 | Gallimore |
| 4,901,355 | A | 2/1990 | Moore |
| 4,902,120 | A | 2/1990 | Weyer |
| 4,904,078 | A | 2/1990 | Gorike |
| 4,943,152 | A | 7/1990 | Whelen |
| 5,020,150 | A | 5/1991 | Shannon |
| 5,029,216 | A | 7/1991 | Jhabvala et al. |
| D325,590 | S | 4/1992 | Galy |
| 5,123,726 | A | 6/1992 | Webster |
| 5,137,342 | A | 8/1992 | Jannard et al. |
| 5,159,639 | A | 10/1992 | Shannon et al. |
| 5,249,001 | A | 9/1993 | Jannard |
| 5,260,997 | A | 11/1993 | Gattey |
| 5,281,957 | A | 1/1994 | Schoolman |
| 5,321,443 | A | 6/1994 | Huber et al. |
| 5,327,178 | A | 7/1994 | McManigal |
| 5,335,285 | A | 8/1994 | Gluz |
| 5,353,378 | A | 10/1994 | Hoffman |
| 5,367,345 | A | 11/1994 | Da Silva |
| 5,381,114 | A | 1/1995 | Pena-Finol et al. |
| 5,404,385 | A | 4/1995 | Ben-Haim |
| 5,406,340 | A | 4/1995 | Hoff |
| RE35,051 | E | 10/1995 | Moore |
| 5,481,763 | A | 1/1996 | Brostrom et al. |
| 5,483,303 | A | 1/1996 | Hirschman |
| 5,483,691 | A | 1/1996 | Heck et al. |
| 5,533,130 | A | 7/1996 | Staton |
| 5,563,951 | A | 10/1996 | Wang et al. |
| 5,579,400 | A | 11/1996 | Ballein |
| 5,581,492 | A | 12/1996 | Janik |
| 5,585,871 | A | 12/1996 | Linden |
| 5,606,743 | A | 2/1997 | Vogt et al. |
| 5,608,808 | A | 3/1997 | Da Silva |
| 5,613,222 | A | 3/1997 | Guenther |
| 5,617,477 | A | 4/1997 | Boyden |
| 5,634,201 | A | 5/1997 | Mooring |
| 5,654,786 | A | 8/1997 | Bylander |
| 5,658,502 | A | 8/1997 | Hughes |
| 5,668,867 | A | 9/1997 | Nagai |
| 5,671,037 | A | 9/1997 | Ogasawara et al. |
| 5,680,465 | A | 10/1997 | Boyden |
| 5,682,434 | A | 10/1997 | Boyden |
| 5,694,475 | A | 12/1997 | Boyden |
| 5,703,670 | A | 12/1997 | Callard |
| 5,708,724 | A | 1/1998 | Burris et al. |
| 5,715,323 | A | 2/1998 | Walker |
| 5,715,337 | A | 2/1998 | Spitzer |
| 5,717,479 | A | 2/1998 | Rickards |
| 5,721,783 | A | 2/1998 | Anderson |
| D392,990 | S | 3/1998 | Hall et al. |
| 5,737,436 | A | 4/1998 | Boyden |
| 5,757,929 | A | 5/1998 | Wang et al. |
| 5,760,868 | A | 6/1998 | Jannard et al. |
| 5,781,272 | A | 7/1998 | Bright et al. |
| 5,796,341 | A | 8/1998 | Stratiotis |
| 5,805,261 | A | 9/1998 | Houston et al. |
| 5,815,126 | A | 9/1998 | Fan |
| 5,835,185 | A | 11/1998 | Kallman et al. |
| 5,853,005 | A | 12/1998 | Scanlon |
| 5,867,572 | A | 2/1999 | MacDonald et al. |
| 5,886,822 | A | 3/1999 | Spitzer |
| 5,889,843 | A | 3/1999 | Singer et al. |
| 5,892,564 | A | 4/1999 | Rahn |
| 5,903,395 | A | 5/1999 | Rallison et al. |
| 5,909,498 | A | 6/1999 | Smith |
| 5,953,000 | A | 9/1999 | Weirich |
| 5,953,434 | A | 9/1999 | Boyden |
| 5,973,728 | A | 10/1999 | Levitan |
| 5,978,689 | A | 11/1999 | Tuoriniemi et al. |
| 5,988,812 | A | 11/1999 | Wingate |
| 5,991,085 | A | 11/1999 | Rallison et al. |
| D418,153 | S | 12/1999 | Haney |
| 6,006,115 | A | 12/1999 | Wingate |
| 6,010,216 | A | 1/2000 | Jesiek |
| 6,012,812 | A | 1/2000 | Rickards |
| 6,013,108 | A | 1/2000 | Karolys et al. |
| 6,018,742 | A | 1/2000 | Herbert, III |
| 6,023,241 | A | 2/2000 | Clapper |
| 6,023,372 | A | 2/2000 | Spitzer et al. |
| 6,030,342 | A | 2/2000 | Amano et al. |
| 6,057,966 | A | 5/2000 | Carroll et al. |
| D426,845 | S | 6/2000 | Green et al. |
| 6,074,060 | A | 6/2000 | Bruce |
| 6,084,555 | A | 7/2000 | Mizoguchi et al. |
| 6,091,546 | A | 7/2000 | Spitzer |
| 6,091,812 | A | 7/2000 | Iglehart et al. |
| 6,091,832 | A | 7/2000 | Shurman et al. |
| D430,145 | S | 8/2000 | Boyden et al. |
| 6,106,116 | A | 8/2000 | Houston et al. |
| 6,108,197 | A | 8/2000 | Janik |
| 6,110,110 | A | 8/2000 | Dublin, Jr. et al. |
| 6,126,595 | A | 10/2000 | Amano et al. |
| 6,142,623 | A | 11/2000 | Jones |
| 6,149,272 | A | 11/2000 | Bergner et al. |
| D435,058 | S | 12/2000 | Green et al. |

(56) References Cited

U.S. PATENT DOCUMENTS

| | | |
|---|---|---|
| 6,157,533 A | 12/2000 | Sallam et al. |
| 6,169,543 B1 | 1/2001 | Wehmeyer |
| 6,176,576 B1 | 1/2001 | Green et al. |
| 6,181,956 B1 | 1/2001 | Koskan |
| 6,192,253 B1 | 2/2001 | Charlier et al. |
| 6,201,629 B1 | 3/2001 | Spitzer |
| 6,204,974 B1 | 3/2001 | Spitzer |
| 6,211,799 B1 | 4/2001 | Post et al. |
| 6,212,414 B1 | 4/2001 | Alameh et al. |
| 6,212,424 B1 | 4/2001 | Robinson |
| 6,218,958 B1 | 4/2001 | Eichstaedt et al. |
| 6,230,327 B1 | 5/2001 | Briand et al. |
| 6,231,181 B1 | 5/2001 | Swab |
| 6,233,344 B1 | 5/2001 | Clegg et al. |
| 6,233,345 B1 | 5/2001 | Urwyler |
| 6,239,778 B1 | 5/2001 | Palffy-Muhoray et al. |
| 6,252,970 B1 | 6/2001 | Poon et al. |
| D445,416 S | 7/2001 | Glezerman |
| 6,272,359 B1 | 8/2001 | Kivela et al. |
| 6,280,838 B1 | 8/2001 | Bernards et al. |
| 6,285,757 B1 | 9/2001 | Carroll et al. |
| 6,301,050 B1 | 10/2001 | DeLeon |
| 6,301,367 B1 | 10/2001 | Boyden et al. |
| 6,301,593 B1 | 10/2001 | Toyosato |
| 6,311,155 B1 | 10/2001 | Vaudrey et al. |
| 6,312,811 B1 | 11/2001 | Frigoli et al. |
| 6,314,091 B1 | 11/2001 | LaRowe, Jr. et al. |
| 6,325,507 B1 | 12/2001 | Jannard et al. |
| 6,325,513 B1 | 12/2001 | Bergner et al. |
| 6,344,727 B1 | 2/2002 | Desai et al. |
| 6,347,095 B1 | 2/2002 | Tang et al. |
| 6,349,001 B1 | 2/2002 | Spitzer |
| 6,350,129 B1 | 2/2002 | Gorlick |
| 6,351,468 B1 | 2/2002 | LaRowe, Jr. et al. |
| 6,353,422 B1 | 3/2002 | Perlman |
| 6,353,503 B1 | 3/2002 | Spitzer et al. |
| 6,356,392 B1 | 3/2002 | Spitzer |
| 6,374,177 B1 | 4/2002 | Lee et al. |
| 6,384,982 B1 | 5/2002 | Spitzer |
| 6,392,798 B1 | 5/2002 | Newkirk |
| 6,409,338 B1 | 6/2002 | Jewell |
| 6,417,969 B1 | 7/2002 | DeLuca et al. |
| 6,421,031 B1 | 7/2002 | Ronzani et al. |
| 6,424,820 B1 | 7/2002 | Burdick et al. |
| 6,431,705 B1 | 8/2002 | Linden |
| D462,708 S | 9/2002 | Miller et al. |
| D462,946 S | 9/2002 | Beraut et al. |
| 6,445,805 B1 | 9/2002 | Grugel |
| 6,452,572 B1 | 9/2002 | Fan et al. |
| 6,456,721 B1 | 9/2002 | Fukuda |
| 6,474,816 B2 | 11/2002 | Butler et al. |
| 6,483,483 B2 | 11/2002 | Kosugi et al. |
| 6,490,362 B1 | 12/2002 | Clegg et al. |
| 6,510,325 B1 | 1/2003 | Mack, II et al. |
| 6,519,475 B1 | 2/2003 | Kim |
| 6,523,006 B1 | 2/2003 | Ellis et al. |
| 6,529,804 B1 | 3/2003 | Draggon et al. |
| 6,538,799 B2 | 3/2003 | Spitzer |
| 6,549,122 B2 | 4/2003 | Depta |
| 6,560,449 B1 | 5/2003 | Liu |
| 6,564,047 B1 | 5/2003 | Steele et al. |
| 6,567,651 B2 | 5/2003 | Whitley |
| 6,580,405 B1 | 6/2003 | Yamazaki et al. |
| 6,582,075 B1 | 6/2003 | Swab et al. |
| 6,614,407 B2 | 9/2003 | Perlman |
| 6,618,099 B1 | 9/2003 | Spitzer |
| 6,629,076 B1 | 9/2003 | Haken |
| 6,639,706 B2 | 10/2003 | Ziv et al. |
| 6,650,894 B1 | 11/2003 | Berstis et al. |
| 6,687,486 B2 | 2/2004 | Grzeczkowski |
| 6,690,807 B1 | 2/2004 | Meyer |
| 6,691,028 B2 | 2/2004 | Bullock et al. |
| 6,717,533 B2 | 4/2004 | Seaberg et al. |
| 6,724,354 B1 | 4/2004 | Spitzer et al. |
| 6,725,022 B1 | 4/2004 | Clayton et al. |
| 6,728,531 B1 | 4/2004 | Lee et al. |
| 6,729,726 B2 | 5/2004 | Miller et al. |
| 6,731,908 B2 | 5/2004 | Berliner et al. |
| 6,733,130 B2 | 5/2004 | Blum et al. |
| 6,735,435 B2 | 5/2004 | Newell et al. |
| 6,763,119 B2 | 7/2004 | Lee |
| 6,766,182 B2 | 7/2004 | Janninck et al. |
| 6,769,767 B2 | 8/2004 | Swab et al. |
| 6,816,314 B2 | 11/2004 | Shimizu et al. |
| 6,834,192 B1 | 12/2004 | Watanabe et al. |
| 6,873,862 B2 | 3/2005 | Reshefsky |
| 6,879,443 B2 | 4/2005 | Spitzer |
| 6,911,172 B2 | 6/2005 | Swab et al. |
| 6,929,365 B2 | 8/2005 | Swab et al. |
| 6,937,400 B2 | 8/2005 | Olsson |
| 6,937,803 B2 | 8/2005 | Bruegl |
| 6,947,014 B2 | 9/2005 | Wooten |
| 6,966,647 B2 | 11/2005 | Jannard et al. |
| 6,975,667 B2 | 12/2005 | Mattisson et al. |
| 6,978,162 B2 | 12/2005 | Russell et al. |
| 7,004,582 B2 | 2/2006 | Jannard et al. |
| 7,013,009 B2 | 3/2006 | Warren |
| 7,044,615 B2 | 5/2006 | Gesten |
| 7,084,736 B2 | 8/2006 | Ritter |
| 7,093,742 B2 | 8/2006 | Steven, III et al. |
| 7,097,300 B2 | 8/2006 | Himmele |
| 7,099,464 B2 | 8/2006 | Lucey et al. |
| 7,106,676 B2 | 9/2006 | Matos |
| 7,124,425 B1 | 10/2006 | Anderson |
| 7,133,532 B2 | 11/2006 | Rickards |
| 7,147,324 B2 | 12/2006 | Jannard |
| 7,149,475 B2 | 12/2006 | Kawamura |
| 7,150,526 B2 | 12/2006 | Jannard |
| 7,158,096 B1 | 1/2007 | Spitzer |
| 7,158,499 B2 | 1/2007 | Anderson et al. |
| 7,162,281 B2 | 1/2007 | Kim |
| 7,185,983 B2 | 3/2007 | Nelson et al. |
| 7,187,948 B2 | 3/2007 | Alden |
| 7,192,136 B2 | 3/2007 | Howell et al. |
| 7,192,137 B2 | 3/2007 | Ishibashi et al. |
| 7,213,917 B2 | 5/2007 | Jannard |
| 7,216,973 B2 | 5/2007 | Jannard |
| 7,219,994 B2 | 5/2007 | Jannard |
| 7,231,038 B2 | 6/2007 | Warren |
| 7,242,527 B2 | 7/2007 | Spitzer |
| 7,253,791 B2 | 8/2007 | Kahan et al. |
| 7,264,350 B2 | 9/2007 | Jannard et al. |
| 7,278,734 B2 | 10/2007 | Jannard et al. |
| 7,289,640 B2 | 10/2007 | Tsai et al. |
| 7,289,767 B2 | 10/2007 | Lai |
| 7,292,703 B2 | 11/2007 | Kaulfuss et al. |
| 7,313,246 B2 | 12/2007 | Miller et al. |
| 7,321,785 B2 | 1/2008 | Harris |
| 7,331,666 B2 | 2/2008 | Swab et al. |
| 7,395,090 B2 | 7/2008 | Alden |
| 7,409,234 B2 | 8/2008 | Glezerman |
| 7,436,568 B1 | 10/2008 | Kuykendall, Jr. |
| 7,438,410 B1 | 10/2008 | Howell et al. |
| 7,445,332 B2 | 11/2008 | Jannard et al. |
| 7,452,073 B2 | 11/2008 | Jannard |
| 7,461,936 B2 | 12/2008 | Jannard |
| 7,484,847 B2 | 2/2009 | Fuziak, Jr. |
| 7,494,216 B2 | 2/2009 | Jannard et al. |
| 7,512,414 B2 | 3/2009 | Jannard et al. |
| 7,581,833 B2 | 9/2009 | Howell et al. |
| 7,631,968 B1 | 12/2009 | Dobson et al. |
| 7,647,400 B2 | 1/2010 | Abbott et al. |
| 7,648,236 B1 | 1/2010 | Dobson |
| 7,675,683 B2 | 3/2010 | Dobson |
| 7,682,018 B2 | 3/2010 | Jannard |
| 7,740,353 B2 | 6/2010 | Jannard |
| 7,744,213 B2 | 6/2010 | Jannard et al. |
| 7,784,935 B2 | 8/2010 | Jackson et al. |
| 7,843,403 B2 | 11/2010 | Spitzer |
| 7,900,068 B2 | 3/2011 | Spitzer |
| 7,967,433 B2 | 6/2011 | Jannard et al. |
| 7,988,283 B2 | 8/2011 | Jannard et al. |
| 8,010,156 B2 | 8/2011 | Warren |
| 8,020,989 B2 | 9/2011 | Jannard et al. |

(56) References Cited

U.S. PATENT DOCUMENTS

| | | |
|---|---|---|
| 8,025,398 B2 | 9/2011 | Jannard |
| 8,086,287 B2 | 12/2011 | Mooney et al. |
| 8,204,435 B2 | 6/2012 | Seshadri et al. |
| 8,313,192 B2 | 11/2012 | Jannard |
| 8,378,924 B2 | 2/2013 | Jacobsen et al. |
| 8,473,004 B2 | 6/2013 | Warren |
| 8,482,488 B2 | 7/2013 | Jannard |
| 8,523,352 B2 | 9/2013 | Jannard et al. |
| 8,550,621 B2 | 10/2013 | Jannard |
| 8,787,970 B2 | 7/2014 | Warren |
| 2001/0009410 A1 | 7/2001 | Fujita |
| 2001/0038491 A1 | 11/2001 | Fergason |
| 2002/0039063 A1 | 4/2002 | Ritter |
| 2002/0044152 A1 | 4/2002 | Abbott, III et al. |
| 2002/0085175 A1 | 7/2002 | Butler et al. |
| 2002/0087330 A1 | 7/2002 | Lee et al. |
| 2002/0093466 A1 | 7/2002 | Ben-Arie |
| 2002/0098877 A1 | 7/2002 | Glezerman |
| 2002/0098878 A1 | 7/2002 | Mooney |
| 2002/0111197 A1 | 8/2002 | Fitzgerald |
| 2002/0118825 A1 | 8/2002 | Mitra |
| 2002/0143912 A1 | 10/2002 | Michels |
| 2002/0159023 A1 | 10/2002 | Swab |
| 2002/0169539 A1 | 11/2002 | Menard et al. |
| 2002/0176330 A1 | 11/2002 | Ramonowski et al. |
| 2002/0186180 A1 | 12/2002 | Duda |
| 2002/0197961 A1 | 12/2002 | Warren |
| 2003/0003969 A1 | 1/2003 | Tong et al. |
| 2003/0022690 A1 | 1/2003 | Beyda et al. |
| 2003/0026586 A1 | 2/2003 | Bruegl |
| 2003/0036360 A1 | 2/2003 | Russell |
| 2003/0058406 A1 | 3/2003 | Blum et al. |
| 2003/0067585 A1 | 4/2003 | Miller et al. |
| 2003/0068057 A1 | 4/2003 | Miller et al. |
| 2003/0073460 A1 | 4/2003 | Van Pelt et al. |
| 2003/0090439 A1 | 5/2003 | Spitzer |
| 2004/0000733 A1 | 1/2004 | Swab et al. |
| 2004/0015403 A1 | 1/2004 | Moskowitz et al. |
| 2004/0029582 A1 | 2/2004 | Swab et al. |
| 2004/0044427 A1 | 3/2004 | Neuhaus |
| 2004/0048569 A1 | 3/2004 | Kawamura |
| 2004/0128399 A1 | 7/2004 | Kurrasch |
| 2004/0132509 A1 | 7/2004 | Glezerman |
| 2004/0156012 A1 | 8/2004 | Jannard et al. |
| 2004/0157649 A1 | 8/2004 | Jannard et al. |
| 2004/0160572 A1 | 8/2004 | Jannard et al. |
| 2004/0160573 A1 | 8/2004 | Jannard et al. |
| 2004/0239874 A1 | 12/2004 | Swab et al. |
| 2005/0041297 A1 | 2/2005 | He et al. |
| 2005/0046789 A1 | 3/2005 | Jannard et al. |
| 2005/0046790 A1 | 3/2005 | Jannard et al. |
| 2005/0128431 A1 | 6/2005 | Jannard et al. |
| 2005/0159182 A1 | 7/2005 | Lai |
| 2005/0174651 A1 | 8/2005 | Spitzer |
| 2005/0185815 A1 | 8/2005 | Rickards |
| 2005/0186993 A1 | 8/2005 | Yueh |
| 2005/0201585 A1 | 9/2005 | Jannard et al. |
| 2005/0202857 A1 | 9/2005 | Seshadri et al. |
| 2005/0208893 A1 | 9/2005 | Yueh |
| 2005/0219152 A1 | 10/2005 | Budd et al. |
| 2005/0248722 A1 | 11/2005 | Nelis |
| 2005/0264502 A1 | 12/2005 | Sprague et al. |
| 2005/0283263 A1 | 12/2005 | Eaton et al. |
| 2006/0009154 A1 | 1/2006 | Tung |
| 2006/0030360 A1 | 2/2006 | Yeh |
| 2006/0034478 A1 | 2/2006 | Davenport |
| 2006/0046656 A1 | 3/2006 | Yang |
| 2006/0072067 A1 | 4/2006 | Jannard |
| 2006/0109350 A1 | 5/2006 | Yeh |
| 2006/0132382 A1 | 6/2006 | Jannard |
| 2006/0146277 A1 | 7/2006 | Jannard |
| 2006/0160573 A1 | 7/2006 | Montvay |
| 2006/0183427 A1 | 8/2006 | Warren |
| 2006/0192306 A1 | 8/2006 | Giller |
| 2006/0197907 A1 | 9/2006 | Jannard |
| 2006/0203183 A1 | 9/2006 | Jannard |
| 2006/0203184 A1 | 9/2006 | Jannard |
| 2007/0008484 A1 | 1/2007 | Jannard |
| 2007/0037520 A1 | 2/2007 | Warren |
| 2007/0046887 A1 | 3/2007 | Howell et al. |
| 2007/0064311 A1 | 3/2007 | Park |
| 2007/0201000 A1 | 8/2007 | Jackson et al. |
| 2008/0013037 A1 | 1/2008 | Carollo |
| 2008/0089545 A1 | 4/2008 | Jannard et al. |
| 2008/0158506 A1 | 7/2008 | Fuziak |
| 2008/0198324 A1 | 8/2008 | Fuziak |
| 2008/0309586 A1 | 12/2008 | Vitale |
| 2009/0073330 A1 | 3/2009 | Viala |
| 2009/0086159 A1 | 4/2009 | Jannard et al. |
| 2010/0238396 A1 | 9/2010 | Jannard |
| 2010/0265455 A1 | 10/2010 | Jannard et al. |
| 2010/0309427 A1 | 12/2010 | Warren |
| 2011/0255050 A1 | 10/2011 | Jannard et al. |
| 2012/0105740 A1 | 5/2012 | Jannard et al. |
| 2013/0281166 A1 | 10/2013 | Warren |
| 2013/0293448 A1 | 11/2013 | Jannard |

FOREIGN PATENT DOCUMENTS

| | | |
|---|---|---|
| CN | 2583696 Y | 10/2003 |
| CN | 1687817 | 10/2005 |
| CN | 2760600 Y | 2/2006 |
| DE | 831 747 C | 2/1952 |
| DE | 202004004378 | 7/2004 |
| EP | 0840465 | 6/1998 |
| FR | 929 851 | 1/1948 |
| FR | 1 444 945 | 10/1966 |
| FR | 2 157 260 | 6/1973 |
| FR | 2642856 | 8/1990 |
| FR | 2 789 499 | 8/2000 |
| GB | 497 375 | 12/1938 |
| GB | 723981 | 2/1955 |
| IT | 00235504 | 4/2000 |
| JP | 42-022998 | 11/1942 |
| JP | 08-036143 | 2/1996 |
| JP | 10-513021 | 12/1998 |
| JP | 11-353444 | 12/1999 |
| JP | 2001-522063 | 11/2001 |
| JP | 2002-085444 | 3/2002 |
| JP | 2003-189398 | 7/2003 |
| WO | WO 96/23373 | 8/1996 |
| WO | WO 97/25790 | 7/1997 |
| WO | WO 97/33270 | 9/1997 |
| WO | WO 99/23524 | 5/1999 |
| WO | WO 99/050706 | 10/1999 |
| WO | WO 00/065803 | 11/2000 |
| WO | WO 00/070390 | 11/2000 |
| WO | WO 00/070779 | 11/2000 |
| WO | WO 00/079329 | 12/2000 |
| WO | WO 00/079333 | 12/2000 |
| WO | WO 01/006298 | 1/2001 |
| WO | WO 02/065198 | 8/2002 |
| WO | WO 03/067585 | 8/2003 |
| WO | WO 03/071830 | 8/2003 |
| WO | WO 2008/076774 | 6/2008 |

OTHER PUBLICATIONS

Alderton, Megan. "The Bluetooth Question", *RF Design*. Jan. 1, 2001.

Bluetooth Specification Version 1.1, Feb. 22, 2001, pp. 1-452.

Borriello, Gaetano. "Survey on Information Appliances", Computer Society, 2002. http://www.computer.org/cga/articles/infoappli.htm, Accessed on Oct. 8, 2003.

De Herrera, Chris. "The Future of the Pocket PC", Pocket PC Magazine, 2003. http://www.pocketpcmag.com/Mar02/future.asp, Accessed on Oct. 8, 2003.

DeVaul et al. "The Memory Glasses: Subliminal vs. Overt Memory Support with Imperfect Information", 2003.

DeVaul, Richard W. "The Memory Glasses Project", MIThril Media Lab, Oct. 28, 2003. http://www.media.mit.edu/wearables/mithril/memory-glasses.html.

(56) References Cited

OTHER PUBLICATIONS

Dorfman, Marjorie. "Wearable Technology: La Com-puter Mo-bile", Byte Back Online, 2003. http://www.bytebackonline.com/Articles_p/wearcomp_p.html, Accessed on Oct. 8, 2003.
"Dressing in Digital Attire", Consumer Electronics Association—Vision, Nov./Dec. 2001. http://www.ce.org/publications/vision/2001/novdec/p08.asp?bc=cat&category_id=39. Accessed on Dec. 5, 2003.
European Office Action in co-pending PCT Application No. 07869181.3 in 4 pages, dated Dec. 7, 2012.
Franklin, Curt. How Bluetooth Works from "www.howstuffworks.com", Web site visited on Jun. 11, 2002.
Frog design and Motorola Launch Prototypes of Next Generation of Wearable Wireless Solutions, *Frog Design.com*, 2003. http://www.frogdesign.com/company/news_press/press_releases/2003/pro046.html. Apr. 5, 2004.
Furan, Amy. "Computing on the Go", Techies.com, Jun. 2000. http://home.techies.com/Common/Career/2.../Verge060100_m.js. Accessed on Oct. 8, 2003.
Hands-Free Profile (HFP), Oct. 22, 2001, 71 pgs.
Headset Profile from Bluetooth Specification Version 1.1, Feb. 22, 2001, pp. 198-224.
Hieb, Barry MD. "The Electronic Age: The Future of Wearables", Advance Newsmagazine—for Nurse Practitioners, Mar. 5, 2001. http://www.advancefornp.com/common/editorial/PrintFriendly.aspx?CC=2160. Accessed on Mar. 17, 2004.
International Preliminary Report on Patentability received in co-pending PCT Application No. PCT/US2007/087309, mailed Jun. 25, 2009, 7 pages.
International Search Report and Written Opinion received in corresponding PCT Application No. PCT/US2007/87309, mailed May 22, 2008, 9 pages.
"Invisible Eyewear Micro Display", *The MicroOptical Corporation*, Pre-2007 publication.
Kleinman, Neil. "Wearable Wear—Wearable computing in jewelry?", Pen Computing—Covering Mobile Computing and Communications. Issue 39, May 2001. http://www.pencomputing.com/wearableware/column39.html. Mar. 17, 2004.
Mann, Steve. "Wearable Computing: A First Step Toward Personal Imaging", Computer—Cybersquare, vol. 30, No. 2, Feb. 1997. http://wearcam.org/ieeecomputer/r2025.htm.
McKay, Niall. "You are What You Wear", The Feature.com, Aug. 7, 2000. http://www.thefeature.com/article?articleid=4223. Accessed on Oct. 8, 2003.
Media, Nando. "Connecting the World through Internet Appliances", Patrickweb.com, Apr. 9, 2000, http://www.patrickweb.com/pages/int.../appliances_iws2000.htm. Accessed on Oct. 8, 2003.
Moran, John M. "Wrist Phones Step Out of the Comic Page", Chicago Tribune Online, Oct. 19, 2000. http://www.chica.../sns-ebiz-wireless101900wrist,0,3250718.stor. Accessed on Oct. 8, 2003.
Motorola Bluetooth Wireless Headset User Guide, 2001, 27 pgs.
Motorola Consumer Catalog for Phone Accessories from "www.commerce.motorola.com", web site visited on Jun. 13, 2002.
"OEM Developer Kits—DV-1 Wireless Digital Viewer", The MicroOptical Corporation—Making Portable Practical. 2004. http://www.microopticalcorp.com/OEM/kitDV-1.html. Accessed on Apr. 20, 2004.
Pentland, Alex Sandy. "Wearable Information Devices", MIT Media Laboratory, pp. 12-67, 2001.
Piller, Charles. "Internet Guru's Theory of Evolution", LA Times.com, Apr. 3, 2000. http://latimes.com/print/business/20000403/t000031121.html, Accessed on Oct. 8, 2003.
Robbins, Alexandra. "A Display in Your Glasses", PC Magazine—The Independent Guide to Technology. Nov. 12, 2002. http://www.pcmag.com/article2/0,4149,667638,00.asp. Accessed on Dec. 5, 2003.
"See What You're Missing—Electronic Images/data are Superimposed Over Your View of the World", Advertisements. The MicroOptical Corporation, Pre-1999 Publication.
Shivers, Olin. "BodyTalk and the BodyNet: A Personal Information Infrastructure", Massachusetts Institute of Technology, Laboratory for Computer Science—Personal Information Architecture Note 1, Dec. 1, 1993.
Special Product Review "ID Magazine", Aug. 2002, p. 179.
Spitzer, Mark B. "The Wristwatch: the bellwether for personal technology", Technology Reports.net, Mar. 26, 2003, http://technologyreports.net/nextinnovator/?articleID=1636. Accessed on Oct. 8, 2003.
Stevens, Cindy Loffler. "A Glimpse into the Digital Future", Consumer Electronics, Mar./Apr. 2000, http://www.ce.org/publications/vision.../pg21.asp?category_id=3. Accessed on Oct. 8, 2003.
"Substance and Style" by Motorola and Frog Design, Motorola. Time Nov. 17, 2003.
Theil, Stefan. "Love Those Wearables!", Newsweek, Apr. 9, 2001. http://nl.newsbank.com/nl-search/we/Archives?p_action=doc&p_docid=0EC05F8D8A26. Accessed on Apr. 15, 2004.
Turoff. "Wearable Computers", Fall 1999 Semester, Course CIS-732, Dec. 16, 1999. http://eies.njit.edu/~turoff/coursenotes/CIS732/sa.../brian_732.html. Accessed on Oct. 8, 2003.
"UDRI Researchers Develop Glasses-mounted Display, Next Generation of Wearable Computers", University of Dayton. Feb. 29, 2000. http://www.udayton.edu/news/nr/022900a.html. Accessed on Dec. 5, 2003.
"The Ultimate Device", Accenture, Nov. 7, 2000. http://www.accenture.com/xd.asp?it=enWeb &xd=Services%5CTechnology%Ctech_ultimate.html. Accessed on Oct. 8, 2003.
"Video glasses come close to melding fantasy, reality", USA Today—Marketplace. http://www.usatoday.com/tech/news/techinnovations/2002-09-23-glasses_x.htm. Accessed on Dec. 5, 2003.
"Wearable Computing", Georgia Institute of Technology, 2003. http://www.gatech.edu/innovations/wearablecomputing. Accessed on Oct. 8, 2003.
Weiss, Peter. "Minding Your Business", Science News Online, Week of May 3, 2003, vol. 16. http://www.sciencenews.org/20030503/bob8.asp. Accessed on Oct. 8, 2003.
Willett, Edward. "Best of Popular Science's What's New: 1999", Edward Willett's Science Columns, 1999. http://www.edwardwillett.com/Columns/popscienceawards99.htm. Accessed on Oct. 8, 2003.
Decision Dismissing Request to Strike Detailed Request for Reexamination, received Jun. 11, 2009 in Reexam U.S. Appl. No. 90/009,088, 5 pages.
Determination of Decision Granting Ex Parte Reexamination, received in Reexam U.S. Appl. No. 90/009,088, Jun. 12, 2008, 14 pages.
Determination of Decision Granting Ex Parte Reexamination, received in Reexam U.S. Appl. No. 90/009,112, Jun. 16, 2008, 14 pages.
Dresang, Joel: "Finns Fluent in Language of Cell Phones", JSOnline—Milwaukee Journal Sentinel, Apr. 15, 2000. http://www.jsonline.com/bym/news/apr00/phone16041500a.asp?format=print. Accessed on Aug. 23, 2004.
European Exam Report, re EPO Application No. 05851915.8, dated Feb. 19, 2013.
European Exam Report, re EPO Application No. 08020604.8, dated Jun. 30, 2011.
European Extended Search Report in co-pending PCT Application No. 07869181.3 in 4 pages, dated Apr. 10, 2012.
European Extended Search Report re EP Application No. 06734820, dated Feb. 11, 2009.
European Extended Search Report re EP Application No. 11171544.7, dated Oct. 7, 2011.
European Extended Search Report, re EPO Application No. 05851915.8, dated Mar. 23, 2011.
European Extended Search Report, re EPO Application No. 08020604.8, mailed Apr. 2, 2009.
European Supplementary Search Report, re EP Application No. 03771935.8, dated Sep. 22, 2009.
Hattori, James: "Bluetooth Developers Aim to Usher in a Wireless Era", CNN.com—Technology—Computing. Sep. 1, 2000. http://cnn.com.

(56) References Cited

OTHER PUBLICATIONS

International Preliminary Report on Patentability, and Written Opinion, re PCT Application No. PCT/US2012/049212, issued Feb. 4, 2014.
International Preliminary Report on Patentability, re PCT Application No. PCT/US05/42084, mailed May 31, 2007.
International Preliminary Report, re PCT Application No. PCT/US03/23472, mailed Sep. 9, 2004, 8 pages.
International Search Report and Written Opinion re PCT Application No. PCT/US06/04860, mailed Aug. 7, 2007, in 10 pages.
International Search Report and Written Opinion, re PCT Application No. PCT/US2012/049212, dated Oct. 22, 2012.
International Search Report, re PCT Application No. PCT/US01/17540, mailed Oct. 26, 2001.
International Search Report, re PCT Application No. PCT/US03/23472, mailed Apr. 20, 2004.
International Search Report, re PCT Application No. PCT/US03/23472, mailed Feb. 12, 2004, 8 pages.
International Search Report, re PCT Application No. PCT/US05/42084, mailed Jan. 16, 2007.
Notice of Intent to Issue Ex Parte Reexamination Certificate, received Jul. 7, 2009 in Reexam U.S. Appl. No. 90/009,088, 10 pages.
Notice of Intent to Issue Ex Parte Reexamination Certificate, received Jul. 7, 2009 in Reexam U.S. Appl. No. 90/009,112, 11 pages.
Office Action (Petition Decision Denying Request to Vacate as Non-Compliant) received in Reexam U.S. Appl. No. 90/009,088, mailed Mar. 11,2009, 16 pages.
Office Action (Petition Decision Denying Request to Vacate as Non-Compliant) received in Reexam U.S. Appl. No. 90/009,112, mailed Mar. 11, 2009, 26 pages.
Patent Owner's Statement under 37 CFR. § 1.530, filed in Reexam U.S. Appl. No. 90/009,088, Aug. 12, 2008, 4 pages.
Patent Owner's Statement under 37 CFR. § 1.530, filed in Reexam U.S. Appl. No. 90/009,112, Aug. 13, 2008, 5 pages.
Petition Decision Denying Request to Vacate as Non-Compliant [37 CFR 1.181(a)&C], received in Reexam U.S. Appl. No. 90/009,112, Mar. 11, 2009, 5 pages.
Petition Decision Denying Request to Vacate as Non-Compliant [37 CFR 1.181(a)&C], received in Reexam U.S. Appl. No. 90/009,088, Jun. 11, 2009, 5 pages.
Petition under 37 CFR. 1.182 to Strike Detailed Request for Reexamination due to Non-Compliance with at Least MPEP 2205, filed in Reexam U.S. Appl. No. 90/009,088, Aug. 12, 2008, 4 pages.
Petition under 37 CFR. 1.182 to Strike Detailed Request for Reexamination due to Non-Compliance with at Least MPEP 2205, filed in Reexam U.S. Appl. No. 90/009,112, Aug. 13, 2008, 4 pages.
Receipt of Original Ex Parte Request by Third Party, Filed in Reexam U.S. Appl. No. 90/009,088, Mar. 20, 2008, 60 pages.
Receipt of Original Ex Parte Request by Third Party, Filed in Reexam U.S. Appl. No. 90/009,112, Apr. 16, 2008, 75 pages.
Reexam Litigation Search conducted in Reexam U.S. Appl. No. 90/009,112, Jul. 1, 2009, 19 pages.
Reexam Litigation Search conducted in Reexam U.S. Appl. No. 90/009,112, Jun. 9, 2008, 14 pages.
Reexam Litigation Search conducted in Reexam U.S. Appl. No. 90/009,112, Mar. 4, 2009, 14 pages.
Reexam Litigation Search conducted in Reexam U.S. Appl. No. 90/099,088, Apr. 9, 2008, 30 pages.
Reexam Litigation Search conducted in Reexam U.S. Appl. No. 90/099,088, Jun. 30, 2009, 19 pages.
Reexam Litigation Search conducted in Reexam U.S. Appl. No. 90/099,088, Mar. 4, 2009, 11 pages.
Wave Report, The Wave Report on Digital Media, Nov. 20, 2000. http://www.wave-report.com/2000%20Wave%20Issues/wave2055.htm, Accessed on Mar. 17, 2004.
Complaint for Patent Infringement; U.S. District—Central District of California; Case No. 03-6284 (GAF)(FMOx); *QR Spex, Inc. and Thomas G. Swab* v. *Motorola, Inc. and Frog Design, Inc.*; filed Sep. 3, 2003; this lawsuit was transferred to the Central District of California from the Eastern District of Texas and was dismissed.
Plaintiffs' Response to Defendant Motorola, Inc.'s First Set of Request for Admission; U.S. District Court—Central District of California; Case No. CV 03-6284 JFW (FMOx); *QR Spex, Inc. and Thomas G. Swab* v. *Motorola, Inc. and Frog Design, Inc.*; dated Mar. 12, 2004; this lawsuit was transferred to the Central District of California from the Eastern District of Texas and was dismissed.
Plaintiffs' Response to Defendant Motorola, Inc.'s First Set of Special Interrogatories; U.S. District Court—Central District of California; Case No. CV 03-6284 JFW (FMOx); *QR Spex, Inc. and Thomas G. Swab* v. *Motorola, Inc. and Frog Design, Inc.*; dated Mar. 12, 2004; this lawsuit was transferred to the Central District of California from the Eastern District of Texas and was dismissed.
Defendant Motorola, Inc.'s Responses to Plaintiffs' First Set of Interrogatories; U.S. District Court—Central District of California; Case No. CV 03-6284 JFW (FMOx); *QR Spex, Inc. and Thomas G. Swab* v. *Motorola, Inc. and Frog Design, Inc.*; filed Apr. 26, 2004; this lawsuit was transferred to the Central District of California from the Eastern District of Texas and was dismissed.
Plaintiffs' Supplemental Response to Defendant Motorola, Inc.'s First Set of Interrogatories; U.S. District Court—Central District of California; Case No. CV 03-6284 JFW (FMOx); *QR Spex, Inc. and Thomas G. Swab* v. *Motorola, Inc. and Frog Design, Inc.*; dated May 18, 2004; this lawsuit was transferred to the Central District of California from the Eastern District of Texas and was dismissed.
Reply Memorandum of Points and Authorities in Support of Defendant Motorola, Inc.'s Motion for Summary Judgment; U.S. District Court—Central District of California; Case No. CV 03-6284 JFW (FMOx); *QR Spex, Inc. and Thomas G. Swab* v. *Motorola, Inc. and Frog Design, Inc.*; filed Jun. 7, 2004; this lawsuit was transferred to the Central District of California from the Eastern District of Texas and was dismissed.
First Amended Complaint for Patent Infringement; U.S. District Court—Central District of California; Case No. SACV 05-1099 AHS (MLGx); *Oakley, Inc.* v. *BMW of North America, LLC.*, filed Nov. 28, 2005; this lawsuit has been settled and dismissed.
First Amended Complaint for Patent Infringment; U.S. District Court—Central District of California; Case No. SACV 06-244 AHS (MLGx); *Oakley, Inc.* v. *Overstock.com, Inc., Wootcom, Inc. dba Synapse Micro, Inc., Global American Technologies, LLC., Aigo, Corp.*, filed Mar. 27, 2006; this lawsuit has been settled in part and dismissed.
First Amended Complaint and Application for Permanent Injuction; U.S. District Court—Eastern District of Texas (Texarkana Division); Civil Action No. 506 CV 124; *QR Spex, Inc.* v. *Motorola, Inc.; Oakley, Inc.; Oakley Sales Corp.; Oakley Direct Inc.; Zeal Optics, Inc.; Xonix Electronic Co., Ltd; and Kyocera Wireless Corp.*, filed Jul. 27, 2006; this lawsuit was transferred to the Central District of California from Eastern District of Texas and was dismissed.
Complaint for Patent Infringement U.S. District—Central District of California; Case No. SACV 06-899 JVS (MLGx); *Oakley, Inc.* v. *Xonix Electronics Co., Ltd.*, filed Sep. 26, 2006; this lawsuit has been dismissed.
First Amended Complaint for Patent Infringement; U.S. District Court—Central District of California, Southern Division; Case No. SACV 07-57 DOC (Anx); *Oakley, Inc.* v. *Blue Diamond International*, filed Jan. 16, 2007; this lawsuit resulted in a default judgment.
Complaint for Patent Infringement; U.S. District Court—Central District of California, SouthernDivision; Case No. SACV 07-558 Ag (RNBx); *Oakley, Inc.* v. *Practical Enterprises, Inc.*, filed May 16, 2007; this lawsuit was settled and dismissed.
Complaint for Patent Infringement; U.S. District Court—Central District of California, Southern Division; Case No. SACV 07-888 CJC (RCx); *Oakley, Inc.* v. *The Pep Boys Manny Moe & Jack of California, Inc.*, filed Aug. 1, 2007; this lawsuit is settled and dismissed.
Stipulation and Amend Pleadings in Consolidated Cases Transferred from Eastern District of Texas; U.S. District Court—Central District of California, Southern Division; Case No. 07-CV-00987 CJC (RNBx); *QR Spex, Inc.* v. *Motorola, Inc. et al.*; filed Sep. 5, 2007; this lawsuit was transferred to the Central District of California from the Eastern District of Texas and was dismissed.
Defendants' Preliminary Invalidity Contentions re U.S. Patent No. 6,769,767, including Exhibit, U.S. District Court-Eastern District of

(56) References Cited

OTHER PUBLICATIONS

Texas; Case No. 5 :06CV124; U.S. District Court, Central District of California; Case No. SACV 06-627 CJC (RNBx); *QR Spex, Inc.* v. *Oakley, Inc., Oakley Sales Corp., Oakley Direct, Inc., and Motorola, Inc.*; This lawsuit is consolidated and dismissed.

Complaint for Patent Infringement; U.S. District Court—Central District of California; Case No. 07-CV-1153 AHS (PJWx); *Oakley, Inc.* v. *Zeal Optics, Inc.*; filed Sep. 28, 2007; this lawsuit was dismissed.

Defendant's Preliminary Invalidity Contentions re U.S. Patent No. 7,331,666 and Addendum, U.S. District Court—Eastern District of Texas; Case No. 5:06CV124; U.S. District Court—Central District of California; Case No. SACV 06-627 CJC (RNBx); *QR Spex, Inc.* v. *Oakley, Inc., Oakley Sales Corp., Oakley Direct, Inc., and Motorola, Inc.*; filed Nov. 3, 2008; this lawsuit was consolidated and dismissed.

Complaint of Patent Infringement; U.S. District Court—Central District of California; Case No. SACV 09-00062 JVS (Anx); *Oakley, Inc.* v. *Spencer Gifts, LLC.*: filed Jan. 14, 2009; this lawsuit was settled and dismissed.

Summons for Complaint for Patent Infringement; U.S. District Court—Central District of California; Case No. CV 09-624 CAS (JWJx); *Oakley, Inc.* v. *Digitalrise, LLC.*; filed Jan. 27, 2009; a default judgment was ordered.

First Amended Complaint for Patent Infringement; U.S. District Court—Central District of California, Southern Division; Case No. SACV 07-671 AG (RNBx); *Oakley, Inc.* v. *Xonix (Zhuhai) Electronics Co., Ltd. et al.*, filed Jun. 7, 2007; this lawsuit was settled and dismissed.

Complaint for Patent and Tradedress Infringement; U.S. District Court—Central District of California; Case No. SA-CV-Jul. 1184 AHS (Anx); *Oakley, Inc.* v. *Audio Visual Allstar dba AVAsunglasses. com*; Filed Oct. 4, 2007; this lawsuit is settled and dismissed.

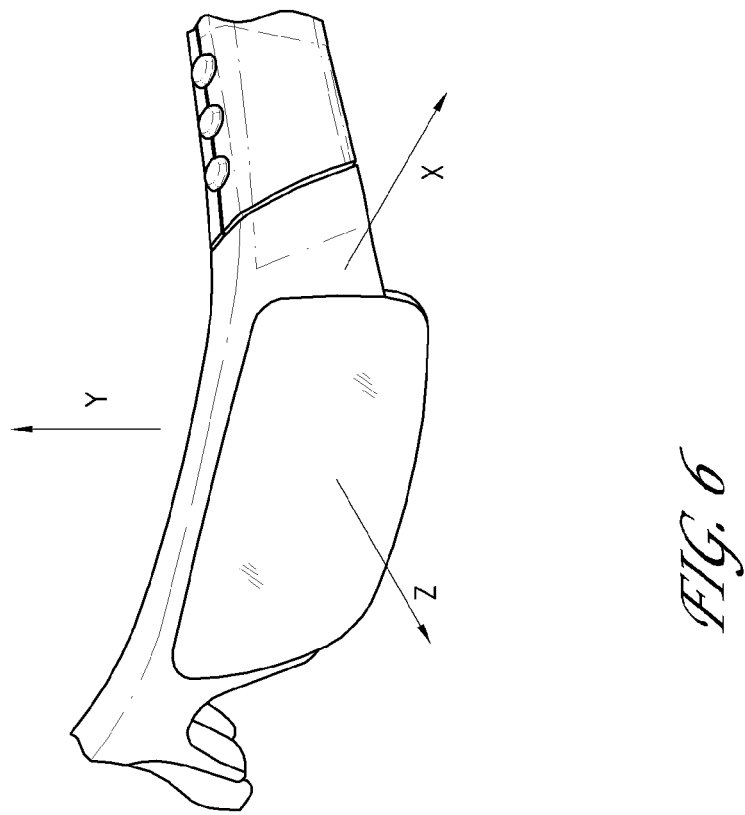
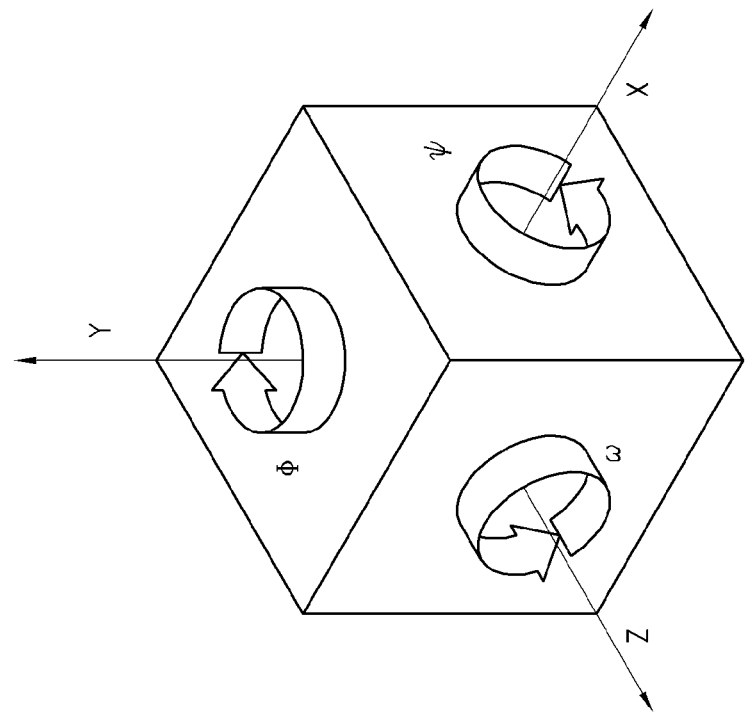
FIG. 6

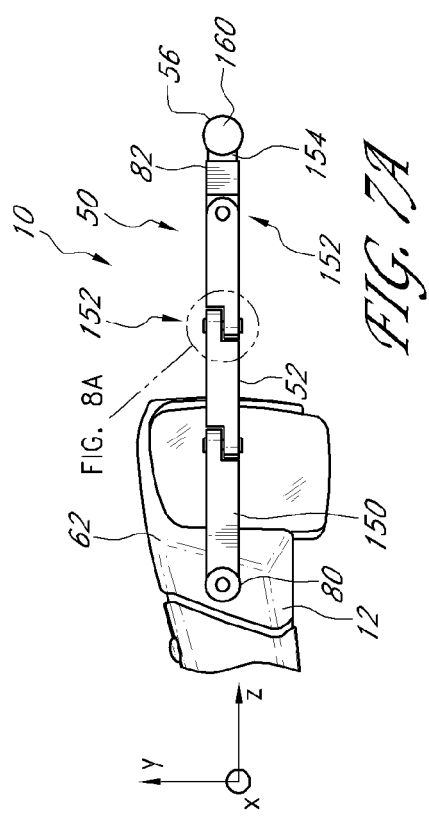
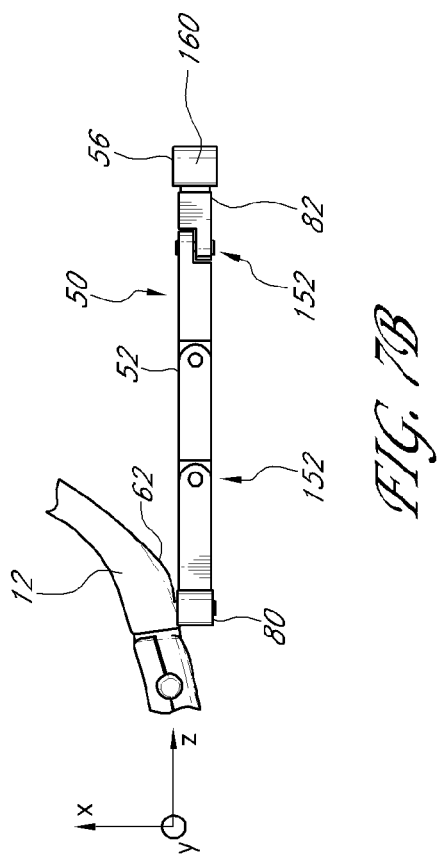
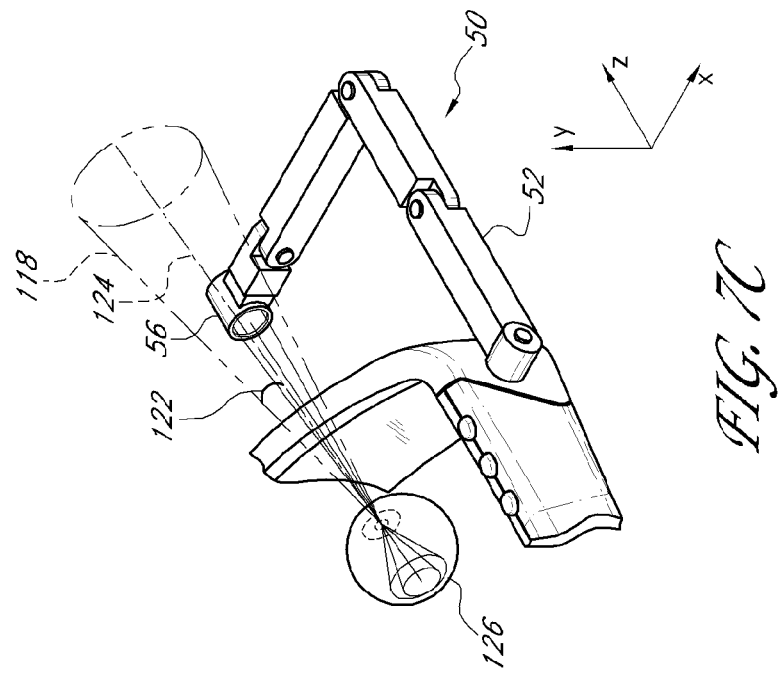
FIG. 7A
FIG. 7B
FIG. 7C

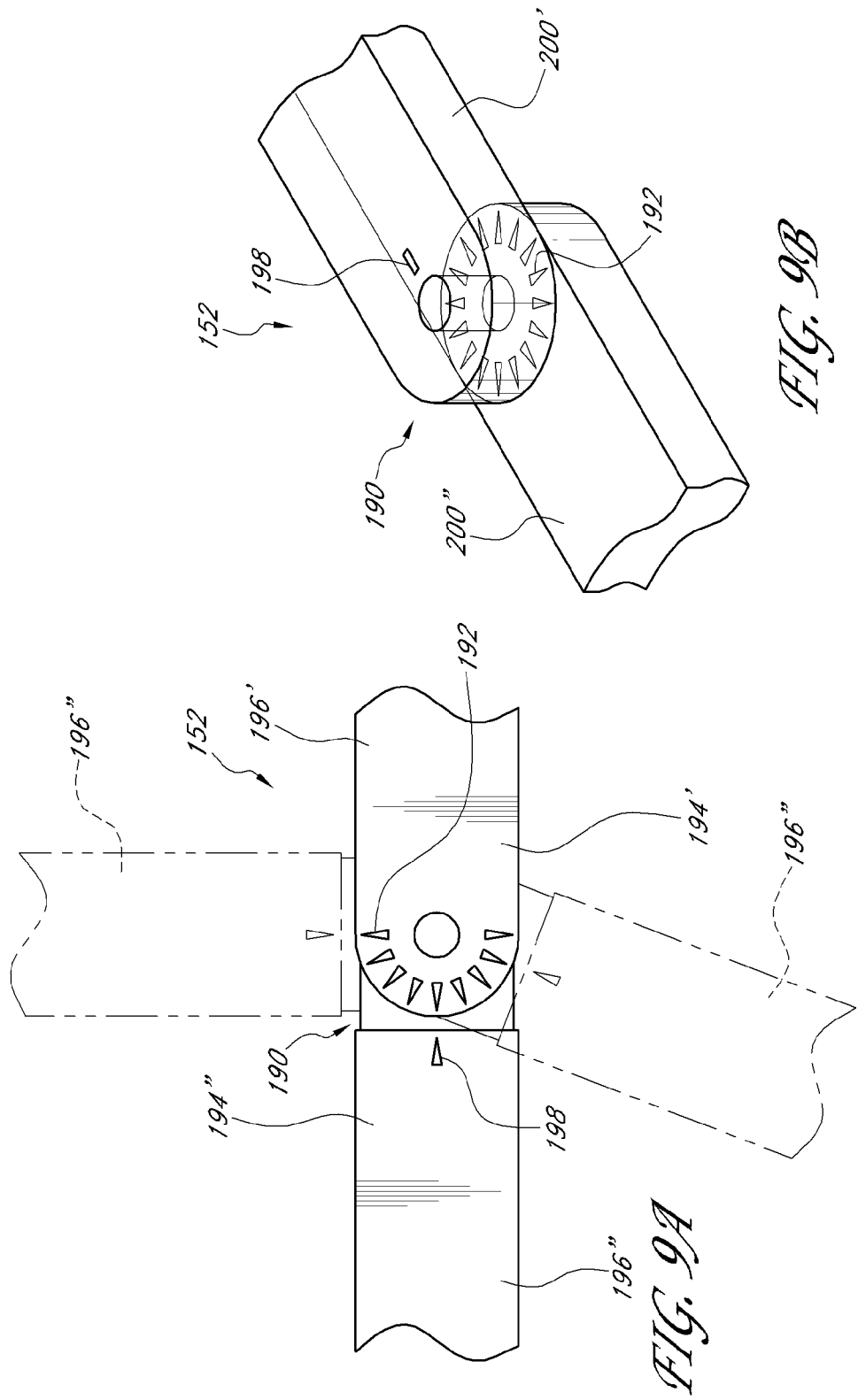

WEARABLE HIGH RESOLUTION AUDIO VISUAL INTERFACE

CROSS-REFERENCE TO RELATED APPLICATIONS

This application is a continuation of U.S. patent application Ser. No. 13/651,999, filed Oct. 15, 2012, now U.S. Pat. No. 8,550,621, which is a continuation of U.S. patent application Ser. No. 13/245,461, filed on Sep. 26, 2011, now U.S. Pat. No. 8,313,192, which is a continuation U.S. patent application Ser. No. 12/820,099, filed on Jun. 21, 2010, now U.S. Pat. No. 8,025,398, which is a continuation of U.S. patent application Ser. No. 11/955,249, filed on Dec. 12, 2007, now U.S. Pat. No. 7,740,353, which claims the benefit of U.S. Provisional Application No. 60/870,064, filed Dec. 14, 2006, the entireties of each of which are incorporated herein by reference.

BACKGROUND

A variety of techniques are available for providing visual displays of graphical or video images to a wearer. In many applications cathode ray tube type displays (CRTs), such as televisions and computer monitors produce images for viewing. Such devices suffer from several limitations. For example, CRTs are bulky and consume substantial amounts of power, making them undesirable for portable or head-mounted applications.

Matrix addressable displays, such as liquid crystal displays and field emission displays, may be less bulky and consume less power. However, typical matrix addressable displays utilize screens that are several inches across. Such screens have limited use in head-mounted applications or in applications where the display is intended to occupy only a small portion of a wearer's field of view. Such displays have been reduced in size, at the cost of increasingly difficult processing and limited resolution or brightness. Also, improving resolution of such displays typically requires a significant increase in complexity.

One approach to overcoming many limitations of conventional displays is a scanned beam display, such as that described in U.S. Pat. No. 5,467,104 of Furness et al., entitled VIRTUAL RETINAL DISPLAY (hereinafter "Furness"), which is incorporated herein by reference. As shown diagrammatically in FIG. 1 of Furness, in one embodiment of a scanned beam display 40, a scanning source 42 outputs a scanned beam of light that is coupled to a viewer's eye 44 by a beam combiner 46. In some scanned displays, the scanning source 42 includes a scanner, such as scanning mirror or acousto-optic scanner, that scans a modulated light beam onto a viewer's retina. In other embodiments, the scanning source may include one or more light emitters that are rotated through an angular sweep.

The scanned light enters the eye 44 through the viewer's pupil 48 and is imaged onto the retina 59 by the cornea. In response to the scanned light the viewer perceives an image. In another embodiment, the scanned source 42 scans the modulated light beam onto a screen that the viewer observes. One example of such a scanner suitable for either type of display is described in U.S. Pat. No. 5,557,444 to Melville et al., entitled MINIATURE OPTICAL SCANNER FOR A TWO-AXIS SCANNING SYSTEM, which is incorporated herein by reference.

SUMMARY

An aspect of at least one of the embodiments disclosed herein includes the realization that despite the development of these and other technologies, there remains a need for a mounting system for adjustably supporting the visual interface optical element or projector with respect to a wearer's field of view.

In some embodiments, an adjustable optical element and assembly can be provided to project at least one optical beam onto a retina of a wearer. The retina of the wearer defines an optical centerline. The optical element can be attachable to a wearable support structure, such as an eyeglass frame, goggle, or other wearable article. The optical element can comprise an adjustable connector, a transmission component, and a transmission surface.

The adjustable connector can have proximal and distal ends. The proximal end can be attachable to the support structure, and the distal end thereof can be adjustable relative to the proximal end. The transmission component can be configured to receive optical data from at least one source module. The transmission component can also be configured to transmit the optical data along a data path toward the distal end of the adjustable connector.

The transmission surface can be disposed on the distal end of the adjustable connector along the data path. The transmission surface can be configured to receive the optical data from the transmission component and to project at least one optical beam onto the retina of the wearer at an angle of incidence relative to the optical centerline. The optical beam can be representative of the optical data. The distal end of the adjustable connector is preferably configured to provide directional movement of the transmission surface along at least X and Y axis for altering the angle of incidence of the optical beam in order to ensure that the optical beam is properly projected onto the retina.

In accordance with one implementation, the transmission surface can be tiltably connected to the distal end of the adjustable connector. The adjustable connector can define a connector axis and the transmission surface can be tiltable about the connector axis. The adjustable connector can also be further configured to provide directional movement of the transmission surface along a Z axis.

In other implementations, the adjustable connector can be configured as a flexible shaft. The adjustable connector can also comprise a plurality of interconnected links. Additionally, the adjustable connector can be adjustable between a plurality of rigid positions. Thus, the adjustable connector can be configured to provide for removable positioning of the transmission surface within a field of view of the wearer. Further, the adjustable connector can be configured to be removably stowable against the wearable support structure.

In accordance with yet other implementations, the transmission surface can project the optical beam onto a reflective surface. In such an embodiment, the beam can be reflected from the reflective surface onto the retina of the wearer.

In yet other implementations, the transmission component can be mounted on the adjustable connector. For example, the transmission component can include an optical fiber.

In accordance with another embodiment, the eyeglass can include a frame and first and second earstems. The frame can define first and second sides, and anterior and posterior portions. The first and second earstems can each define outer and inner portions. The first and second earstems can be connectable to the respective ones of the first and second sides of the frame. In this regard, first and second optical elements can be connected to the eyeglass, and each of the first and second optical elements can correspond to a respective one of left and right eyes of the wearer.

In such an embodiment, the optical elements can be attachable to the eyeglass to produce a variety of potential assemblies. For example, each proximate end of each of the first and second optical elements can be connected to the respective ones of the outer portions of the left and right earstems of the eyeglass. Alternatively, each proximate end of each of the first and second optical elements can be connected to the anterior portion of the frame of the eyeglass. Furthermore, each proximate end of each of the first and second optical elements can be connected to the posterior portion of the frame of the eyeglass.

In accordance with yet another embodiment, each adjustable connector can include at least one orientation indicator for allowing symmetrical positioning of the first and second adjustable connectors. In yet another embodiment, each adjustable connector can comprise a plurality of links, and each link can include the orientation indicator for allowing symmetrical positioning of each respective link of the first and second adjustable connectors.

BRIEF DESCRIPTION OF THE DRAWINGS

The above-mentioned and other features of the inventions disclosed herein are described below with reference to the drawings of the preferred embodiments. The illustrated embodiments are intended to illustrate, but not to limit the inventions. The drawings contain the following figures:

FIG. 6 is a perspective view of an eyeglass illustrating the x, y and z coordinate axes, as well as respective pitch, yaw and roll movements about the axes for illustrating exemplary directions in which the optical element can be adjusted according to an embodiment.

FIG. 7A is a side view of the optical element according to another embodiment.

FIG. 7B is a top view of the optical element depicted in FIG. 7A.

FIG. 7C is a rear perspective view of the optical element illustrated in FIG. 7A and further illustrating projection of the optical beam onto the retina of the eye of the wearer, according to another embodiment.

FIG. 9A is a top view of links of the adjustable connector including an orientation indicator, in accordance with an embodiment.

FIG. 9B is a top view of links of the adjustable connector wherein a link is see-through corresponding to an orientation indicator, in accordance with yet another embodiment.

DETAILED DESCRIPTION

Figure 1:
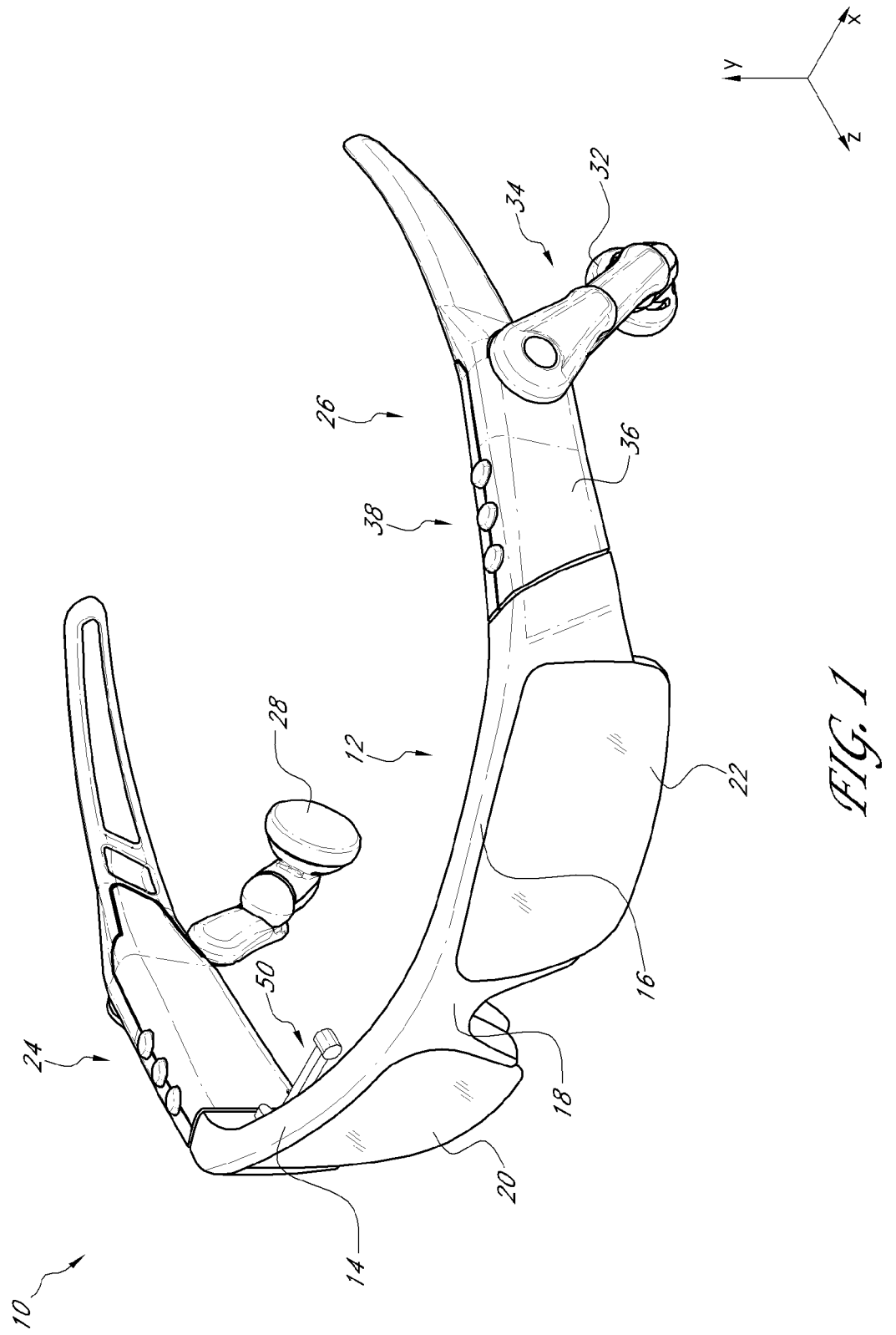
FIG. 1 is a front perspective view of a projection assembly including an eyeglass, an audio output capability and a visual output capability provided by at least one adjustable optical element, in accordance with an embodiment.

The inventions herein described provide a portable visual display capability to a wearable article. Although described below primarily in combination with an eyeglass frame, the adjustable visual optical element can be readily incorporated into any of a variety of alternative support structures. For example, in addition to any of a variety of eyeglass configurations including plano or prescription sunglasses or prescription waterwhite eyeglasses, embodiments of the adjustable optical element may be carried by goggles, such as ski goggles, or motorcycle motocross goggles, military goggles, industrial safety glasses or goggles, or other protective eyewear. Alternatively, the visual optical element may be carried by any of a variety of articles typically worn on the wearer's head, such as headphones, earphones, a hat, helmet, mask, visor, headband, hair band or the like as will be apparent to those of skill in the art in view of the disclosure herein. The optical alignment of the optical element can be adjustable and locked at the point of sale or selectively adjustable by the wearer.

The adjustable optical element can be configured to deliver visual information to the eye. This may be accomplished by projecting an image or other data directly on the retina, or by displaying an image on a surface within the wearer's field of view. The optical element may be driven by any of a wide variety of source electronics, either carried on board the eyeglasses, or in communication with the eyeglasses from a remote source either via hard wiring or wireless communication.

In general, source electronics may include a computing and/or memory device, such as a computer, a server, a network, drive, RAM, ROM or other non-removable or removable memory chip. The source electronics may alternatively comprise a digital audio visual player, such as an MP3 player, an ipod, or a multi-media player such as a portable DVD player, or other visual or audio visual memory media which may be developed. The source electronics can also accommodate a high band wireless connection for both audio and video, and can include an onboard chipset to control the incoming wireless a/v, volume, etc.

The source electronics may alternatively comprise any of a variety of radiofrequency transmission sources such as a terrestrial based or satellite based radio, cellular telephone, or customized wireless signal source. A personal digital assistant (PDA), a blackberry, pager, or any of a variety of alternative PDA's and email enabled devices, notebook computers, or other devices capable of generating a visual (e.g. text and/or image) signal may also be used to drive the optical element.

In alternate embodiments, the source electronics may include any of a variety of devices capable generating a visual text, alpha numeric or still frame or moving image output. For example, time measuring devices such as clocks or timers, or sensors for measuring a body biometric, such as wearer's pulse, temperature, or blood parameters such as blood oxygen saturation, blood glucose level, or blood pressure may be used. The sensor may be configured to provide an alarm, or a signal indicative of a time or a sensed biometric to a wearer when certain threshold levels are measured, or at periodic intervals. Such thresholds and periodic intervals may be selected or programmed by the wearer, or may be preset.

In other embodiments, the sensor of the source electronics may measure distance or determine positional location. For example, the source electronics may provide a visual image including information derived from a Global Positioning System (GPS) or an altimeter. Such sensors may be used to determine the distance from an object, including the distance from a location, distance traveled from a starting point, or the distance to a target. Such distance sensor may also be configured to provide an alarm, or a signal indicative of a distance to a wearer when certain threshold levels are measured, or during periodic intervals.

The source electronics may provide a visual indicium of any of a variety of time varying parameters, such as speed, acceleration, or jerk (e.g. the rate of change in acceleration). The source electronics may provide a visual signal indicative of an instantaneous or an average time varying parameter at fixed or at wearer selected intervals. For example, in one embodiment, the source electronics incorporates a GPS receiver and position indicating electronics to provide a display of a map as well as an indicator of the location of the wearer on the map.

The source electronics may be external to the wearable electronic interface, in which case a communication link is provided to electronically couple the source electronics with the optical element. The communication link may be either a direct electrical coupling (for example hard wiring, or inductive coupling through the body), or a wireless protocol.

Wireless source electronics may be infrared enabled or radiofrequency communication enabled, such as Bluetooth enabled. For example, in one embodiment, the source includes a Bluetooth enabled transmitter for either video or audio and video signals. The source electronics may alternatively comprise a hand held device, such as a night vision scope, telescope with optical and/or digital zoom, or digital camera for still photos or cinematography.

As mentioned above, the optical element can be utilized in combination with a wearable article. In this regard, the wearable article may include various types of support structures that can be worn on the head or torso of a wearer. However, it is also contemplated that the optical element can be utilized in combination with other structures that are not worn by the wearer.

For example, the optical element can be mounted on a structure so as to position the optical element to properly facilitate the use of the optical element, such as on a headrest of a seat or other similar structure with respect to which the wearer's head is frequently oriented. However, as illustrated in the figures, the optical element is described in the context of a pair of eyeglasses, and more specifically, in the context of a dual lens pair of eyeglasses. Furthermore, according to various embodiments, other capabilities can be incorporated into the support structure, such as audio and/or tactile feedback capabilities.

Referring now to FIG. 1, a projection assembly is provided that includes a support structure, such as an eyeglass 10 with a frame 12 which comprises a first orbital 14 and a second orbital 16 connected by a bridge 18. The first orbital can support a first lens 20, and the second orbital 16 can support a second lens 22. As is understood in the eyeglass arts, the first and second orbitals 14, 16 can surround the entirety of the corresponding lens, or only a portion of the lens, sufficient to support the lens in the wearer's field of view. Frameless configurations may also be used, although a frame may be desirable if wires are needed to extend between the left and right ear stems. As an alternative to separate first and second lenses 20, 22, the eyeglass 10 can be provided with a single, unitary lens, which extends throughout the entire desired range of vision of both the wearer's right and left eyes.

A first earstem 24, and a second earstem 26 can be connected to the frame 12. Preferably, each earstem is hingably or movably connected to the frame 12, to enable folding as is understood in the art. However, a hingeless frame can alternatively be used.

In an embodiment wherein the eyeglass 10 is provided with audio capability, a first earstem 24 can be used to support a first speaker 28 by way of a first speaker support 30. Preferably, the first speaker support 30 is adjustable such as by construction from a flexible material or structure, or an articulating structure as will be discussed in greater detail below. In an embodiment configured for stereo sound or dual mono-sound, a second speaker 32 is preferably supported by the second earstem 26, by way of a second speaker support 34.

As will be discussed in greater detail below, one or both of the first and second earstems 24, 26 can house electronics 36 necessary for the operation of the audio capability of the eyeglass 10 and/or the visual display capabilities, described below. The electronics 36 can be provided with any of a variety of controls 38, such as dials, push buttons, switches or other such controls depending upon the desired functionality. Further, as described in greater detail below, the electronics 36 can be in electrical or optical communication with at least one transmission component 40 for providing the visual display capability of the assembly.

In an embodiment configured to direct retinal projection, at least one optical element 50 is operative to project at least one optical beam onto a retina of the wearer. As such, the optical element 50 is in optical and/or electrical communication with the electronics 36 which provide the optical element 50 with optical image data that is utilized to produce the optical beam. The optical element 50 can include the transmission component 40, as described below.

The optical beam projected by the optical element is representative of the optical image data and can be transmitted to the retina of the wearer through a variety of optical and electrical components as known in the art.

Figure 2:
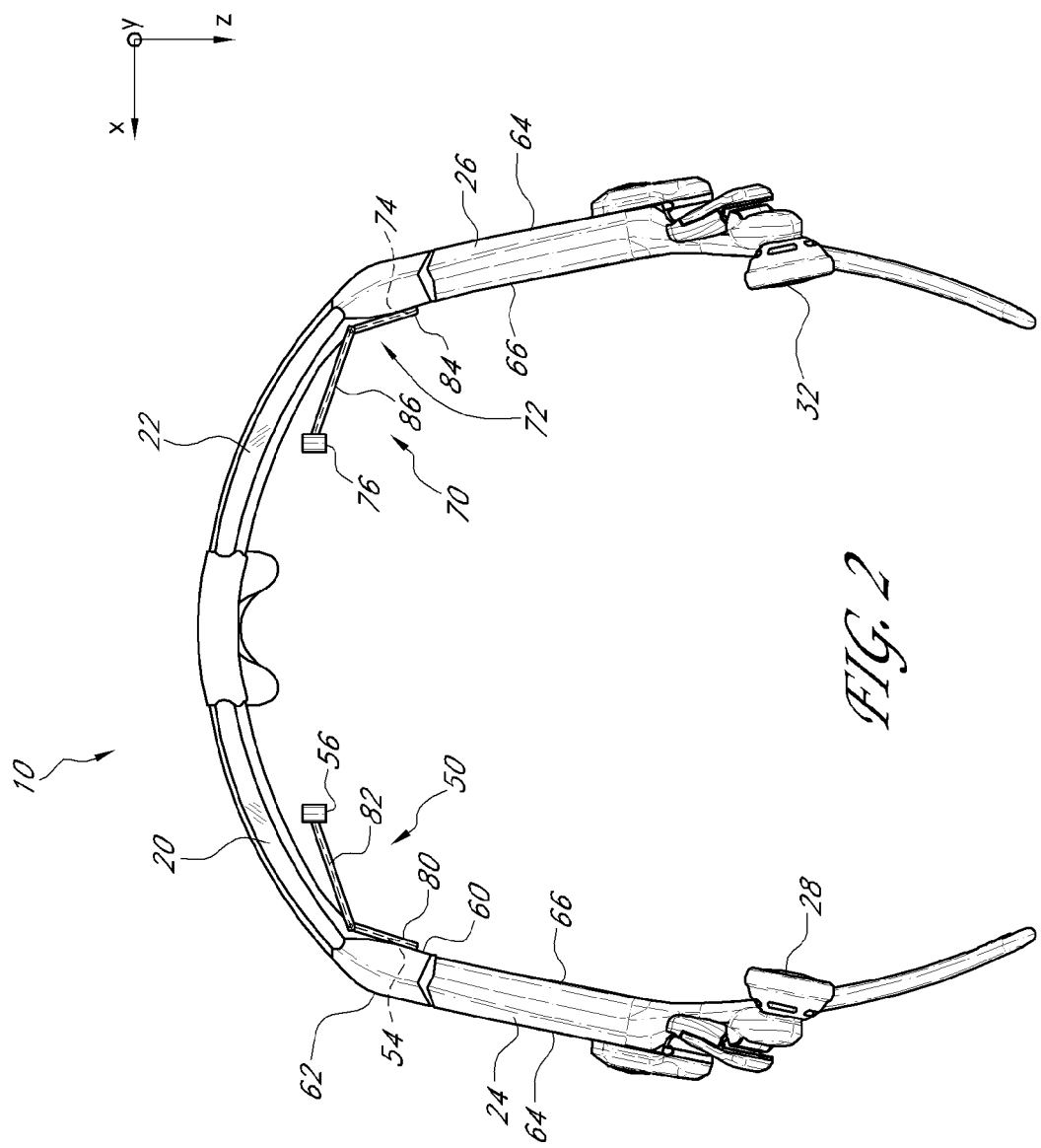
FIG. 2 is a bottom plan view of the embodiment illustrated in FIG. 1 showing first and second adjustable optical elements of the projection assembly.

Referring now to FIG. 2, there is illustrated a bottom plan view of the eyeglass 10 illustrated in FIG. 1. According to various embodiments discussed herein, the optical element 50 can be a first optical element 50 that is adjustably positionable within the wearer's right eye field of view. The first optical element 50 comprises an adjustable connector 56, a first transmission component 53, and a first transmission surface 54. The first transmission surface 54 can be directed towards the eye of the wearer or towards the first lens 20 or other image reflecting surface. In this regard, the optical beam projected by the optical element 50 can be directly projected toward the eye of the wearer or can be reflected toward the eye of the wearer such as by reflection off of the first lens 20. Furthermore, the optical element can be utilized in conjunction with electrochromic or photochromic lenses for indoor/outdoor viewing.

The optical element 50 can be mounted on either a posterior portion 60 or an anterior portion 62 of the frame 12, relative to the lens. Alternatively, the optical element can also be mounted along lateral portion 64 or medial portion 66 of either of the first or second earstems 24, 26. Thus, the frame 12 can be positioned intermediate the eye of the wearer and the optical element, or the optical element can be positioned intermediate the eye and the frame 12. Such configurations can be provided in response to whether direct or indirect projection of the optical beam is desired, and other design or desired performance criteria. In an implementation, the first optical element 50 can be paired with, used in combination with, and/or used separately from a second optical element 70. Similar to the first optical element 50, the second optical element 70 can also include a second adjustable connector 72, a second transmission component 74, and a second transmission surface 76.

Although various embodiments illustrated herein depict the use of both first and second optical elements 50, 70, it is contemplated that embodiments can utilize a single optical element, and that the optical element can also incorporate various combinations of the features discussed herein. For purposes of simplifying the present description, it is noted that where the optical element is referred to in singular form, such as the first optical element 50 or the second optical element 70, the described features can also be incorporated into the other one of the first and second optical elements 50, 70. Therefore, reference to the first optical element 50 alone should not be construed as limiting. Additionally, as mentioned above, it is contemplated that the first optical element 50 can be used alone, and therefore, embodiments can incorporate one or two optical elements, as desired.

Referring now to FIG. 2, the first and second optical elements 50, 70 can be adjustably supported on the eyeglass 10, by first and second adjustable connectors 52, 72, respectively. As discussed herein, and as illustrated in the accompanying figures, the first and second adjustable connectors 52, 72 can be provided in a variety of configurations and can incorporate various useful features, as desired. In a simple embodiment, the first and second adjustable connectors 52, 72 can comprise any of a variety of flexible support elements, articulating arm elements, telescopic elements, or other extension structures. The flexible support elements can be simple gooseneck supports or other supports as described further below.

The first adjustable connector 52 can have a proximal end 80 and a distal end 82, and the second adjustable connector 72 can have a proximal end 84 and a distal end 86. As illustrated in FIG. 2, the proximal ends 80, 82 of the respective ones of the first and second adjustable connectors 52, 54 can be attached to a support structure, such as the frame 12. In this regard, the first and second adjustable connectors 50, 52 can comprise any of a variety of structures that can permit the distal ends 84, 86 to be adjustable relative to the respective ones of the proximal ends 80, 82.

As mentioned above, certain implementations may utilize a single optical element 50 for projecting the optical beam to one of the right or left eyes of the wearer. Depending on the application, use of a single optical element may be sufficient. However, in embodiments where the optical beam is preferably directed to both of the wearer's eyes, the second optical element 70 can also be used. As such, as illustrated in FIG. 2, the first optical element 50 can be adjustably positioned within the wearer's right eye field of view while the second optical element 70 can be adjustably positioned within the wearer's left eye field of view.

The electronics 36 utilized by the optical element can incorporate a variety of components and can be variously modified by one of skill in the art using present and prospective knowledge related to retinal projection and related technologies in accordance with implementations.

Figure 3:
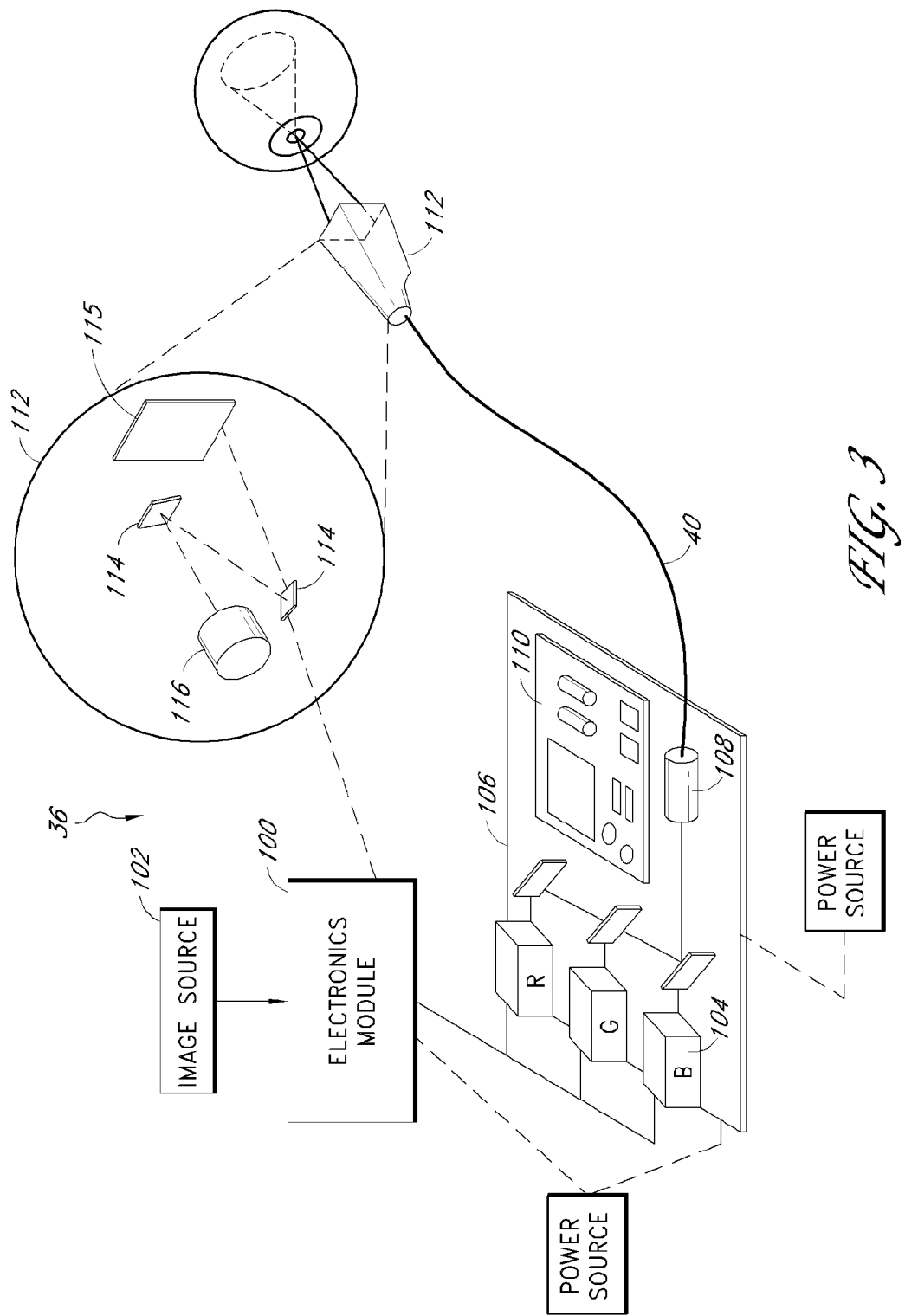
FIG. 3 illustrates exemplary electronics used in the optical element for providing retinal projection of an image onto the retina of a wearer.

For example, as illustrated in the embodiment of FIG. 3, the electronics 36 can include an electronics module 100 that receives image data from an image source 102. The image data can include information utilizable to create an image, such as placement and intensity of color in the image. The electronics module 100, as is known in the art, can be used to decipher the image data such that it can be optically portrayed by the electronics 36. In this regard, the electronics 36 can also include various light sources 104, color combining optics 106, a photonics module 108, and modulators 110. These components can be in electronic communication with the electronic module 100 and receive the deciphered imaged data therefrom and create the image based on the deciphered image data.

The light sources 104 can paint the image in RGB and be modulated and combined utilizing the color combining optics 106, the photonics module 108, and the modulators 110. Finally, a scanner module 112, which can be mounted on the optical element, can project the optical beam onto the retina of the wearer in order to raster scan or "paint" the optical image onto the retina. In this regard, the scanner module 112 can include various micro electro-mechanical structures such as scanners 114, a diffuser 115, and a focusing lens 116. Preferably, the image is painted in RGB at the rate of at least approximately 30 times per minute for premium resolution. However, other scanning rates can also be used.

As mentioned above, embodiments can be favorably implemented in combination with various electronics 36; it is also contemplated that with the advance of science, new and improved electrical and optical components can become available and be incorporated into embodiments. Furthermore, the optical beam can be directly or indirectly projected toward the eye of the wearer. Therefore, although FIG. 3, as well as other figures, illustrate direct retinal projection, it is contemplated that the optical beam can be reflected off of other structures incorporated into the optical element, such as the first and second lenses 20, 22 of the eyeglass 10 or other reflective surface.

In accordance with some embodiments, the scanner module 112, as discussed above, can be incorporated into the optical element and be configured to provide the optical beam which is projected toward the eye of the wearer. Thus, the first and second transmission surfaces 56, 76 of the first and second optical elements 50, 70 can each be configured to include the scanner module 112. As such, the first and second transmission surfaces 56, 76 can project the optical beam toward the eye of the wearer within an angular range of allowability.

In addition, as mentioned above, the optical element 50 can also be formed to include the transmission component 40. The transmission component 40 can communicate the image data from the light sources 104 to the scanner module 112. In some embodiments, the transmission component 40 can be mounted on the adjustable connector 52, and can include an optical fiber or waveguide. However, it is also contemplated that where the scanner module 112 is separate from the first and second transmission surfaces 56, 76, the transmission component 40 may not be disposed on the adjustable connector, as described below.

However, although embodiments can provide that the first and second transmission surfaces 56, 76 include the scanner module 112, it is also contemplated that the scanner module 112 can be separate from the first and second transmission surfaces 56, 76. For example, it is contemplated that the first and second transmission surfaces 56, 76 can include at least one optical mirror that optically communicates with the scanner module 112 to project the optical beam onto the retina.

Figure 4:
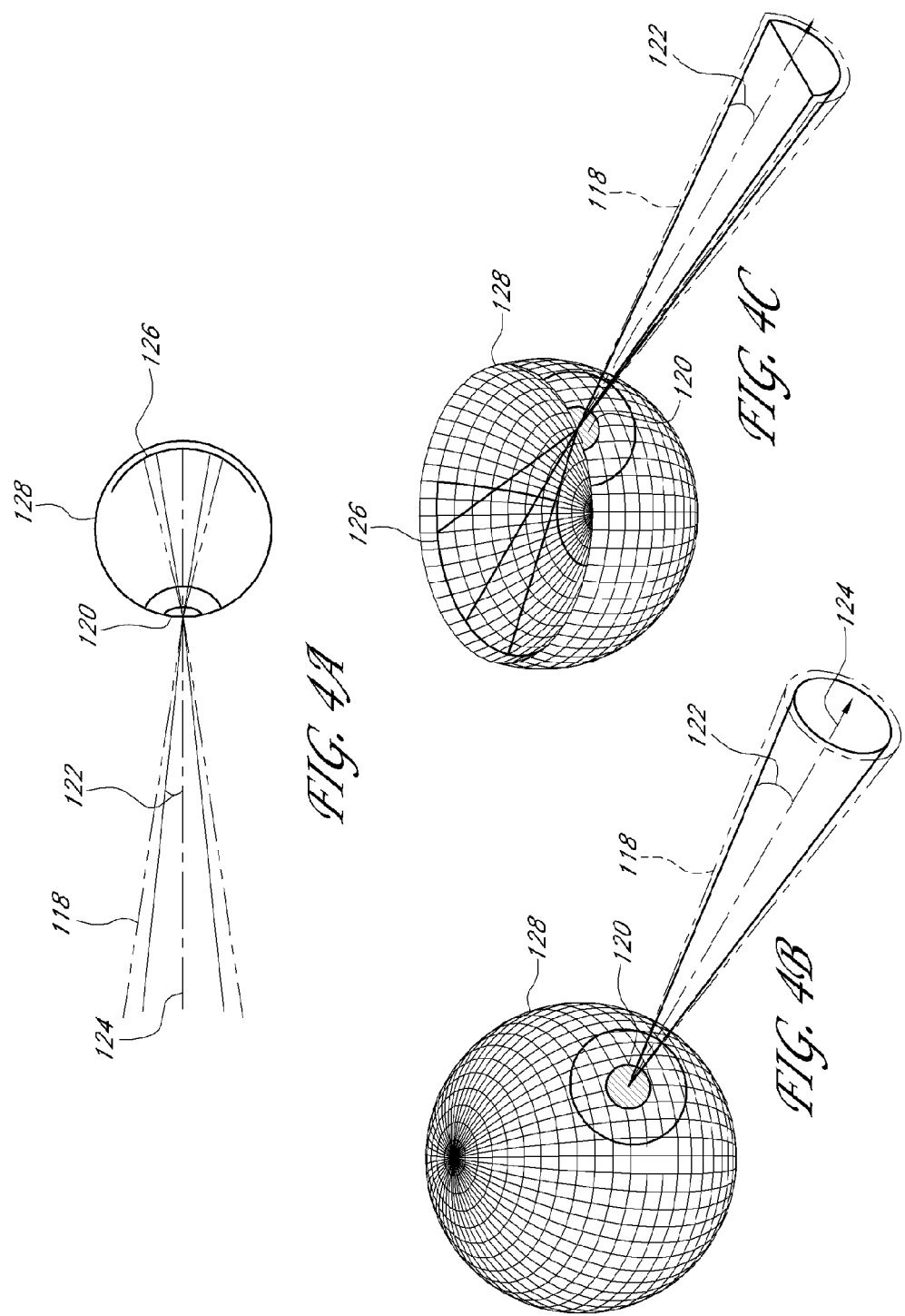
FIG. 4A is a side cross-sectional view of the eye illustrating an optical center line, an angle of incidence of an optical beam, a range of allowability, and a retina, in accordance with an embodiment.
FIG. 4B is a perspective view of the eye illustrating the optical center line, the range of allowability, and the angle of incidence, in accordance with an embodiment.
FIG. 4C is a perspective view of a horizontal cross-section of the eye depicted in FIG. 4B.

Referring now to FIGS. 4A-C, the eye of the wearer is schematically illustrated. As is known in the optical arts, the retina of the eye serves as an exit pupil for light entering the eye. The eye includes a pupil 120 that serves as an exit pupil for the eye of the wearer. Light entering the pupil of the eye can be focused onto the retina of the eye, where the focused light excites rods and cones of the retinal tissue and consequently causes detection and transmission of an image to the brain. Such capabilities and the operations of the human eye are basically known in the art. In retinal projection technology however, an image is scanned onto the retina of the wearer by the scanner module 112. The scanner module 112 can implement a raster scanning of the optical beam in order to "paint" the image onto the retina of the wearer.

According to embodiments, the raster scanning of the optical beam onto the retina of the wearer can be optimized when the transmission surface 56 projects the optical beam at an angle of incidence 122 that falls within the range of acceptance 118. The range of acceptance 118 can be defined as the maximum angular displacement of the optical beam with respect to an optical center line (OCL) of the retina 126. Since the absolute orientation of the OCL will vary as the eye moves, embodiments can normally be designed with the assumption that the OCL is aligned in the normal, straight ahead viewing position. Thus, retina projection can be optimized by ensuring that the optical beam is projected onto the retina 126 within the range of acceptance 118. Such can ensure that the optical beam reaches the retina 128 and is therefore detectible and utilizable in forming a perceivable image.

FIG. 4A illustrates a side cross-sectional view of the eye 128 illustrating the optical center line 124 intersecting the retina 126. The angle of incidence 122 is depicted as falling within the range of acceptance 118 in order to allow the optical beam to be properly projected onto and detected by the retina 126 of the wearer. While FIG. 4A illustrates a vertical cross-sectional side view, FIG. 4B illustrates that the range of allowability 118 extends also in the horizontal direction. Thus, according to an implementation, the optical beam is preferably projected onto the retina 126 within a range of acceptance 118, which can be conical in shape. The cone is centered about an axis, such as a normal straight ahead line of sight. However, although the range of acceptance 118 is three-dimensionally depicted as being conical, the optimal range of acceptance may not be precisely conical due to a variety of factors.

FIG. 4C illustrates a horizontal cross-sectional view of the eye 128 wherein the range of acceptance 118, the angle of incidence 122, and the optical center line 124 are each depicted. Retinal projection can be optimized in embodiments by ensuring that the optical beam projected by the transmission surface 56 is projected onto the retina of the wearer at an angle of incidence 122 that falls within the range of acceptance 118. The angle of incidence 122 can be defined as the angle measured between the optical beam and the optical center line 124. The angle of incidence 122 is generally no greater than about 40° and in certain embodiments no greater than about 20°.

Figure 5:
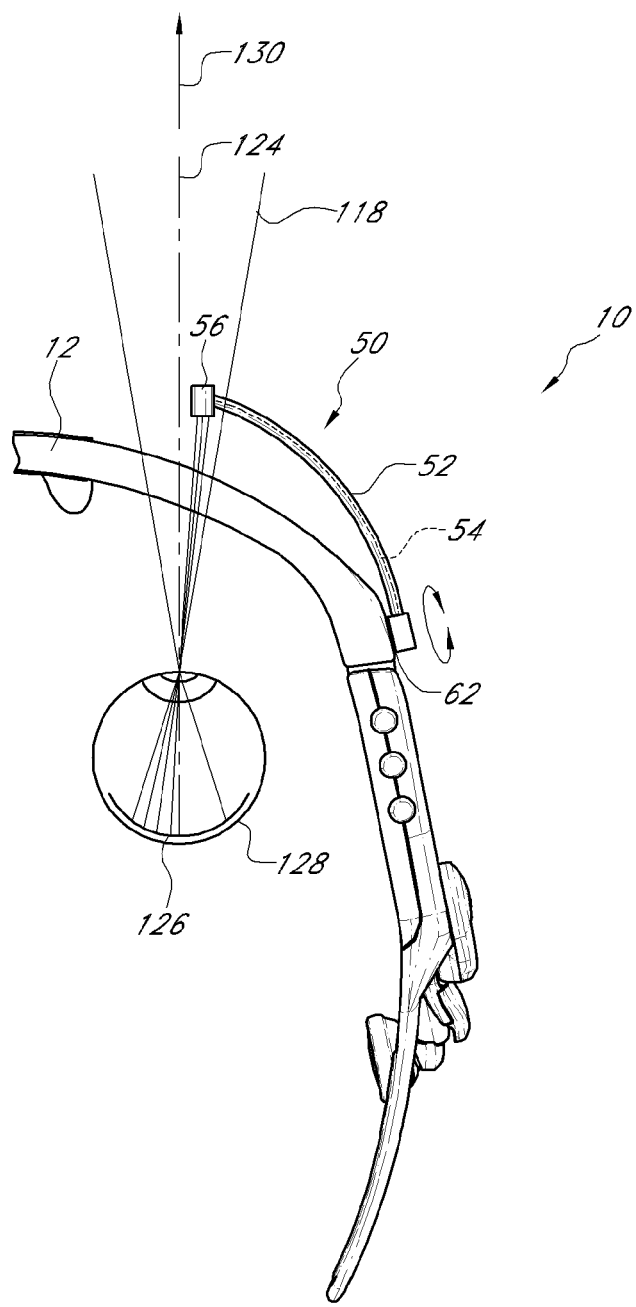
FIG. 5 is a top plan view of an assembly illustrating the placement of the optical element within the wearer's right field of view and within the range of allowability.

Referring now to FIG. 5, a top plan view of the eyeglass 10, the first optical element 50, and the eye 128 of the wearer is illustrated. The transmission surface 56 should be positioned within the right eye field view of the wearer such that the optical beam is projected onto the retina 126 of the eye 128 within the range of acceptance 118. The transmission surface 56 can be positioned within in the A-P axis outside of an "eyelash zone" of the eye, which zone can be radially measured as extending approximately as far as the eyelashes of the wearer. Such positioning can be implemented where the optical element is disposed on the posterior portion 62 of the frame 12, as shown in FIGS. 1-2.

The positioning of the transmission surface 56 with respect to the eye 128 can affect the apparent size of the image produced by the optical beam scanned onto the retina 126. Thus, the first adjustable connector 52 can be adjusted as required in order to produce an image of desired size. Furthermore, the transmission surface 56 can also be adjusted in order to properly focus the image onto the retina 126.

While FIG. 5 illustrates that the first optical element 50 can be attached to the anterior portion 62 of the frame 12, the first optical element 50 can likewise be attached to the posterior portion 60 of the frame 12. Furthermore, FIG. 5 illustrates that the optical center line 124 can be substantially aligned with the wearer's straight ahead line of sight 130. The straight ahead line of sight can be defined as that line that extends longitudinally forward from the eye 128 of the wearer. Because the eyes of the wearer can be moved relative to the head of the wearer and therefore allow the wearer to look in different directions while the head is maintained stable, the straight ahead line of sight 130 shall refer to the longitudinal line of sight that projects forwardly from the head.

The embodiment illustrated in FIG. 5 illustrates that the optical center line 124 can be substantially aligned with the straight ahead line of sight 130. However, embodiments are not limited to positioning the transmission surface 56 within a range of allowability defined by the straight ahead line of sight 130. Instead, it is also contemplated that the transmission surface 56 can be laterally positioned relative to the eye such that when the eye is rotated, for example, to the right, the transmission surface 56 would then fall within the range of allowability 118 in order to allow the optical element to "paint" the image onto the retina of the wearer. Therefore, although embodiments contemplate that the optical center line 124 is substantially collinear with the straight ahead line of sight 130, it is also contemplated that other uses of the optical element can be made such as to allow the wearer to selectively access the retinal projection or in other words, allow the retina projection to take place.

Referring now to FIG. 6, there is provided an illustration of X, Y, and Z coordinate axes, in which directions the adjustable connectors 52, 72 can be selectively adjusted. In addition, FIG. 6 also illustrates other directional movements of the adjustable connector 52, 72 in the pitch (identified by the Greek letter ψ), yaw (identified by the Greek letter φ), and roll (identified by the Greek letter ω) directions. Each of the directions of movement illustrated in FIG. 6 also represents a respective degree of freedom. The term "degree of freedom" can be used to refer to movement in any of three translational directions or three rotational directions. Translational movement can take place in the direction of any of the X, Y, or Z axis. Rotational movement can take place about any of the X, Y, or Z axis, as respectively illustrated by the Greek letters ψ, φ, and ω.

It is contemplated that the various embodiments of the optical element can be adjustable in several, if not all, of the directions illustrated in FIG. 6. Although such adjustability could be advantageous, it is not a required feature for various embodiments. Thus, several of the embodiments disclosed herein can advantageously incorporate directional movement in at least two or three of the directions shown in FIG. 6.

The first and second adjustable connectors 52, 72 can be variously configured in order to provide adjustability of the respective ones of the first and second transmission surfaces 56, 76. FIGS. 7A-C illustrate one embodiment of the adjustable connector 52, as shown on a like side of the eyeglass 10. As shown in FIG. 7A, the proximate end 80 of the first adjustable connector 52 can be pivotally attached to the frame 12 of the eyeglass 10. Although the proximate end 80 is illustrated as being attached to a central position of the anterior portion 62 of the frame 12, it is contemplated that the proximal end 80 can be attached in a variety of other configurations. For example, instead of being vertically pivotally attached, the proximate end 80 can be horizontally pivotally attached, or rigidly attached, and/or removably attached to the anterior portion 62 of the frame 12.

The first optical element 50 can be configured such that the distal end 82 of the adjustable connector 52 is adjustable relative to the proximate end 80 thereof. In this regard, adjustment of the distal end 82 likewise provides for the adjustability of the transmission surface 56 in order to ensure that the optical beam can be optimally projected on to the retina of the wearer. The adjustability of the first optical element 50 can be accomplished through a variety of structures, such as those embodiments illustrated herein. For example, FIGS. 7A-B illustrate that the adjustable connector 52 can be comprised of one or more links 150. The links 150 can be interconnectable in an end-to-end fashion and can provide for several degrees of freedom of movement of the adjustable connector 52. In addition, the adjustable connector 52 can be configured to provide telescoping capability, be detachable, and be hollow or otherwise provide a slot wherein wiring can be installed if necessary.

The embodiment of the adjustable connector 52 illustrated in FIGS. 7A-B can include a plurality of interconnected links 150 that provide numerous degrees of freedom to the adjustable connector 52. As shown in FIG. 7C, with the various degrees of freedom, the adjustable connector 52 can enable the optical element 50 to be properly positioned such that the transmission surface 56 can project the optical beam on to the retina 126 of the wearer at an angle of incidence 122 that is within the range of allowability 118. Thus, utilizing the various degrees of freedom of the adjustable connector 52, the transmission surface 56 can be properly positioned to project the optical beam within the range of acceptability 118.

As illustrated in FIGS. 7A-B, each of the links 150 can be configured to mate with a respective link 150 at a link joint 152. As shown, the link joints 152 can be configured to allow the adjustable connector 52 to pitch about the X axis or to yaw about the Y axis.

Further, the optical element 50 can also be configured to include a transmitter joint 154 that is disposed intermediate the distal end 82 of the adjustable connector 52 and the transmission surface 56. In some embodiments, the transmission surface 56 can be housed in a transmitter 160 that is disposed at the distal end 82 of the adjustable connector 52. In some implementations, the transmitter joint 154 can allow the transmitter 160 to rotate with respect to the distal end 82 of the adjustable connector 52. Therefore, depending upon the orientation and attitude of each link joint 152 and the transmitter joint 154, the optical element 50 can be adjusted to a desired orientation, as shown in FIG. 7C, in order to properly position the transmission surface 56 to project the optical beam on to the retina 126 at an angle of incidence 122 within the range of acceptability 118.

Figure 8A:
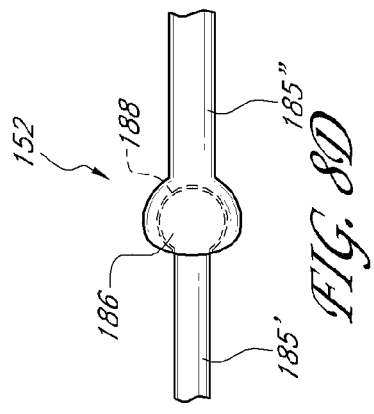
FIG. 8A is a side view of two links used in an adjustable connector of the optical element, in accordance with yet another embodiment.
Figure 8C:
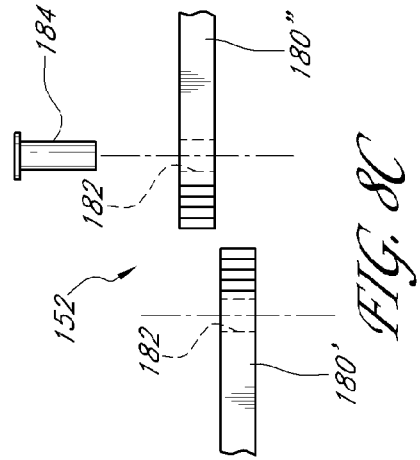
FIG. 8C is a side view of links of the adjustable connector in accordance with yet another embodiment.
Figure 8B:
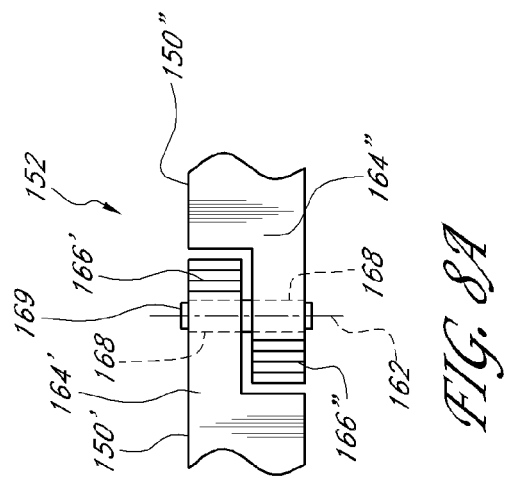
FIG. 8B is a side view of links of the adjustable connector in accordance with another embodiment.

Referring now to FIGS. 8A-8C, an embodiment of the link joint 152 shown in FIG. 7A-B is provided in greater detail. FIG. 8A shows the link joint 152 in an assembled configuration where links 150' and 150" interconnect to provide pivotal motion of the adjustable connector 52 about a link axis 162. As shown in FIG. 8A, each link 150', 150" can include a distal end 164', 164", the distal ends 164', 164" can be configured to include mating steps 166', 166". In accordance with an implementation, the mating steps can each include an axial passage through which a fastener, such as a rivet, bolt, or screw can be inserted to interconnect the lengths 150', 150".

Referring now to FIG. 8B, another embodiment of the link joint 152 is illustrated. As shown in FIG. 8B, the lengths 170, 170' can be configured to include additional mating steps 172', 172". Although the mating steps 172', 172" can be similarly configured to include an axial passage similarly shown in FIG. 8A, it is contemplated that the mating step 172' can include opposing axial projections 174 that are sized and configured to be received within receiving cavities 176 of the mating steps 172". In this regard, according to an embodiment, the link 170' can be rotatably coupled to the link 170" through the insertion of the projections 174 into the receiving cavities 176. According to an implementation, the projections 174 can be axially aligned with respect to each other and with respect to the receiving cavities 176 in order to provide pivotal movement of the link 170' relative to the link 170" at the link joint 152.

According to yet another embodiment, FIG. 8C illustrates a simplified link joint 152 wherein link 180' and link 180" can each be configured to be substantially planar in shape. Further, the links 180', 180" can each be and configured to include an axial passage 182 through which a connector 184 can be inserted to pivotally couple length 180' to link 180" at a link joint 152. Such an embodiment can be advantageous because it can allow link 180' to pivot fully with respect to link 180", thus not having its rotational movement restricted as may be the case in the embodiments illustrated in FIGS. 8A-B.

Figure 8D:
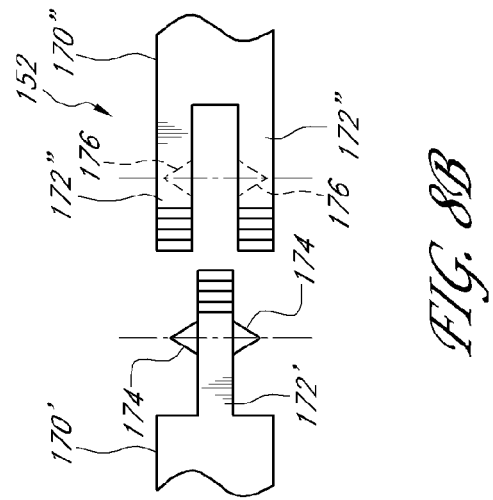
FIG. 8D is a side view of links of the adjustable connector in accordance with yet another embodiment.

In accordance with yet another embodiment, the link joint 152 can be configured to provide ball-and-socket interconnection between adjacent links 185', 185", as illustrated in FIG. 8D. For example, the link 185' can be formed to include a spherical male end 186 that is receivable within a receiving end 188 of the adjacent link 185". This ball-and-socket embodiment of the joint link 152 can allow for multi-directional movement of the link 185' with respect to the adjacent link 185". Such a configuration can also be advantageous over other configurations noted in FIGS. 8A-C. Furthermore, it is contemplated that other ball-and-socket connections can be implemented in order to provide the advantageous qualities described herein.

Referring now to FIGS. 9A-B, it is also contemplated that the optical element 50 can include an orientation indicator 190 that allows the wearer to determine the orientation of the optical element 50 with respect to the support structure. The term "orientation indicator" can be used to refer to at least one orientation indicator disposed on a portion of the optical element 50, or to refer to several indicators used in combination to collectively provide information related to the orientation of the optical element 50 as positioned with respect to the support structure.

The orientation indicator can be useful for a variety of purposes. For example, in an embodiment of the optical element 50, the adjustable connector 52 can be configured to be adjustable between a nested position and an extended position, as described herein. In the nested position, the optical element could be compactly nested in order to facilitate storage of the optical element. In such an embodiment, the optical element can be configured to be removably attached to the structure such that the optical element, once removed, is adjusted to its nested position in order to facilitate storage of the optical element.

Alternatively, and as discussed further herein, the optical element 50 can be storable or nested on the support structure itself. In such an embodiment, the optical element 50 can be adjusted to its nested position when not in use.

In either of the above-mentioned embodiments, the optical element 50 can be adjusted from its nested position to its extended position and the orientation indicator 190 can be used to facilitate the quick and repeatable positioning of the optical element to the extended position. For example, the orientation indicator 190 can be inspected by the wearer after the optical element 50 has been adjusted into a proper extended position wherein the optical beam is projected onto the retina within the range of allowability. Then, the wearer can visually inspect the orientation indicator 190 so that the wearer can learn precisely how the adjustable connector 52 should be oriented to facilitate quick and repeatable adjustment of the optical element 50 to the extended position at which the optical element 50 is effective.

As shown in FIG. 9A, the orientation indicator 190 can include a plurality of radially extending markings 192 disposed on a distal end 194' of a link 196'. Additionally, a guide marking 198 can be disposed on a distal end 194" of an adjacent link 196". The embodiment illustrated in FIG. 9A can correspond to either of the link joints 152 illustrated in FIG. 8A or 8B. According to an implementation, the orientation indicator 190 can comprise both the plurality of markings 192 and the guide marking 198. In one embodiment, the plurality of markings can include letters, numbers, or other alpha-numeric digits. As shown in FIG. 9A, the plurality of markings 192 can simply include radially extending lines, which can be configured to be of varying lengths. The plurality of markings 192 is preferably configured to be easily read and perceived by the wearer. In addition, the guide marking can also comprise any of a variety of alpha-numeric characters, symbols or other shapes that can be used to point to or otherwise correspond to one of the plurality of markings 192 in a given orientation. As illustrated in FIG. 9A, the adjacent link 196" can be rotatably adjusted with respect to the link 196', and the guide marking 198 can be used to allow the wearer to visually adjudge the orientation of the adjacent link 196" with respect to the link 196'.

Referring now to FIG. 9B, another embodiment of the orientation indicator 190 is shown. In such an embodiment, at least an upper link 200' can be made at least partially of a see-through material, such as a transparent, translucent or otherwise clear plastic. The link joint 152 illustrated in FIG. 9B can correspond to the link joint 152 illustrated in FIG. 8C. The upper link 200' can mate with a lower link 200" to form the link joint 152.

Similar to the embodiment illustrated in FIG. 9A, the orientation indicator 190 shown in FIG. 9B can also include the plurality of markings 192 and at least one guide mark 198. Because the upper link 200' is see-through, it is contemplated that the plurality of markings 192 and/or the guide marking 198 can be selectively disposed on either of the upper link 200' and/or the lower link 200". As such, when adjusting the adjustable connector 52 of the optical element 50, the wearer can refer to the orientation indicator 190 in order to adjudge the relative positioning of the links 200', 200". It is contemplated that various other embodiments can be implemented utilizing these teachings.

In accordance with yet another embodiment, it is contemplated that the first and second optical elements 50, 70 can each have an orientation indicator 190. In such an embodiment, the adjustable connectors 52, 72 can be symmetrically positioned with respect to each other by use of the orientation indicators 190. Such an embodiment can tend to ensure that the optical beams projected from the transmission surfaces 56, 76 of the respective ones of the first and second optical elements 50, 70 approach the eye at similar angular orientations. In this regard, a visual echo can be avoided, or at least the optical beams can be oriented closely enough such that the brain simply blends the images provided by the optical beams. Therefore, as discussed further below, the first optical element 50 can be adjusted to be in a perfect minor image location relative to the second optical element 70, in accordance with an embodiment.

Figure 10C:
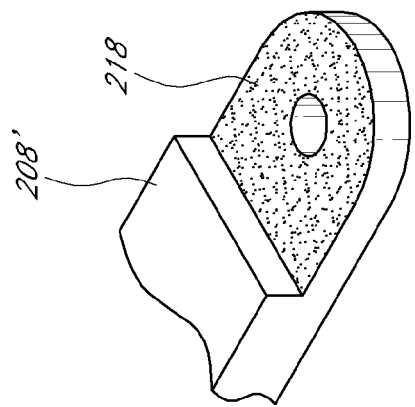
FIG. 10C is a perspective view of a link including a frictional surface for providing ridged engagement with an adjacent link in accordance with yet embodiment.
Figure 10B:
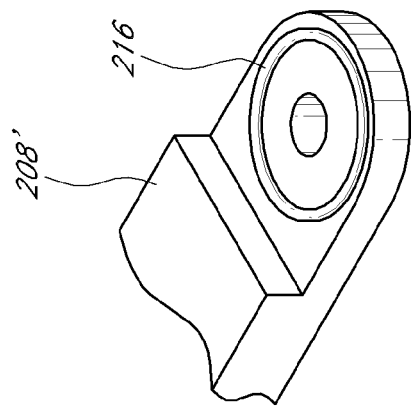
FIG. 10B is a perspective view of a link including a rubber ring for providing ridged engagement between an adjacent link in accordance with yet another embodiment.
Figure 10A:
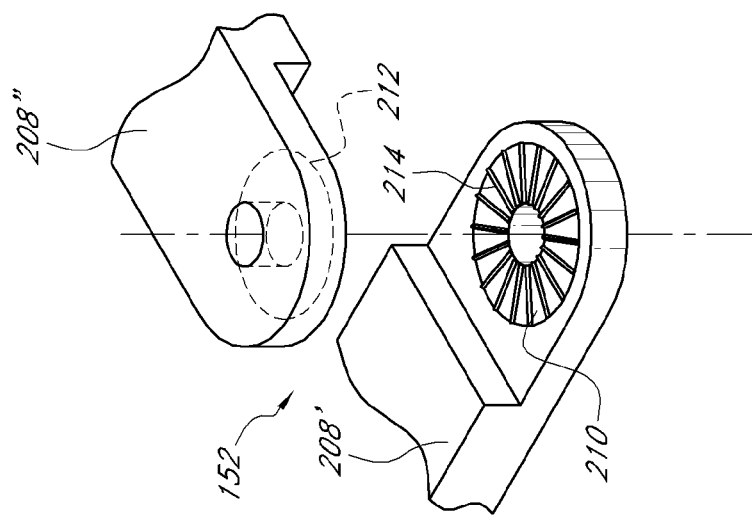
FIG. 10A is a perspective view of links of the adjustable connector illustrating ridges for providing ridged engagement between the links in accordance with an embodiment.

Referring now to FIGS. 10A-C, the optical element 50 can also be configured with the adjustable connector 52 being adjustable between a plurality of rigid positions. The rigid positions of the adjustable connector 52 can refer to a discrete plurality of orientations at which the adjustable connector 52 is in a substantially fixed or immobile state. Therefore, according to implementations, the adjustable connector 52 can provide adjustability and lockout for the optical element 50.

FIGS. 10A-C also illustrate that the link joint 152 can be configured such that at least one link 208' includes an engagement surface 210 that provides frictional engagement with a mating surface 212 of the adjacent link 208". It is contemplated that the engagement surface 210 can include at least one ridge 214 (as illustrated in FIG. 10A), a rubber engagement ring 216 (as illustrated in FIG. 10B), and/or a frictional coating 218 (as illustrated in FIG. 10C), or other types or combinations of geometries or materials that can allow the link 208' to be rigidly positioned with respect to the link 208".

In such an embodiment, rigid positioning can be accomplished through a friction-based engagement or through mating geometries of the engagement surface 210 and the mating surface 212. Further, the mating surface 212 can likewise be configured to include the geometries and/or materials mentioned with respect to the engagement surface 210. In particular, the mating surface 212 can preferably be configured to correspond to the engagement surface 210 in providing a rigid engagement between the links 208', 208". For example, the contour and shape of the mating surface 212 can correspond to that of the engagement surface 210, such as each including a plurality of ridges.

In accordance with yet another embodiment, the optical element 50 can be configured with the transmission surface 52 being tiltably connectable to the distal end 882 of the adjustable connector 52. Exemplary embodiments of such a configuration are illustrated in FIGS. 11A-C.

Figure 11A:
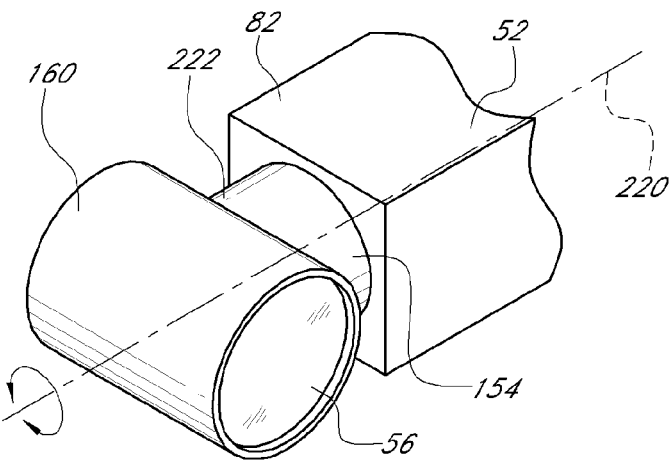
FIG. 11A is a perspective view of the optical element illustrating tiltability of a transmission surface in accordance with an embodiment.

Referring first to FIG. 11A, the distal end 82 of the adjustable connector 52 can define a connector axis 220. The connector axis 220 can be defined as extending longitudinally from the distal end 82 of the adjustable connector 52. As illustrated in FIG. 11A, the transmission surface 56 can be configured to rotate about the connector axis 220. This rotational movement can be facilitated through the use of a rotation connector 222. The rotation connector can rotatably couple the transmission surface 256 to the distal end 82 of the adjustable connector 52. As illustrated in FIG. 11A, the rotation connector 222 can be positioned at the transmitter joint 154. In such an embodiment, the rotation connector can interconnect the transmitter 160 directly to the distal end 82 of the adjustable connector 52.

Figure 11B:
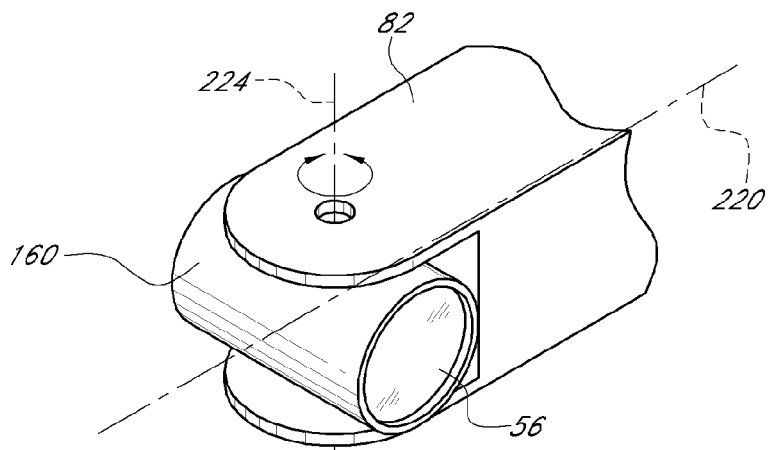
FIG. 11B is a perspective view of the optical element illustrating the pivotability of the transmission surface in accordance with yet another embodiment.

According to another implementation, the optical element 50 can also be configured to allow the transmission surface 56 to rotate transversely to the connector axis 220, as illustrated in the embodiment shown in FIG. 11B. The transmission surface 56 can define a transmitter axis 224, as illustrated in FIG. 11B. The distal end 82 of the adjustable connector 52 can be configured to provide rotatable interconnection with the transmitter 160 such that the transmitter 160 and the transmission 56 can rotate about the transmitter axis 224. In the embodiment illustrated in FIG. 11B, the transmitter axis 224 can be transversely oriented with respect to the connector axis 220. Thus, the transmission surface 56 can be configured to rotate or swivel about the transmitter axis 224.

Figure 11C:
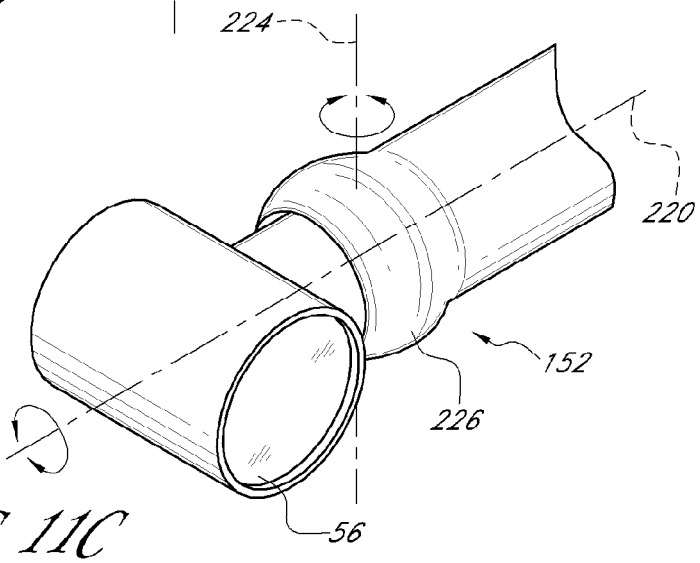
FIG. 11C is a perspective view of the optical element illustrating the tiltability and rotatability of the transmission surface in accordance with yet another embodiment.

In yet another embodiment, the transmission surface 56 can be rotatable about the transmitter axis 224 and tiltable with respect to the connector axis 220, as illustrated in the embodiment of FIG. 11C. As shown therein, the link join 152 can be configured to provide a ball-and-socket connection 226 that can allow the transmission surface 56 to rotate about the connector axis 220 and the transmitter axis 224. In addition, the ball-and-socket connection 226 can also allow the transmission surface 56 to be at least partially translidable in each of the X, Y, and Z axial directions.

Various other configurations can be implemented in order to allow the transmission surface 56 to be tiltable with respect to the connector axis 220 and/or rotatable with respect to the transmitter axis 224. Such configurations can be prepared utilizing the teachings herein in combination with skill in the art. For example, the optical element can be configured such that it is capable of tracking along the surface of a sphere. Further, the optical element can also be configured to track along an exterior surface of the lens.

As mentioned above with respect to FIG. 5, the optical element(s) can be connected to the anterior portion 62 of the frame 12 or to the outer portion 64 of the earstem(s). Further, the optical element(s) can also be connected to the posterior portion 60 of the frame 12 or to the inner portion 66 of the earstem(s). Further, it is contemplated that the optical element(s) can be configured to be nestable within a portion of the frame 12 or earstems 24, 26 as desired. Thus, the optical element(s) can be moveable between a nested position and an extended position. Such a design may provide a sleek and unobtrusive nested configuration. For example, the connectors can be configured to fold against the earstems, and various types of link joints can be used to allow the adjustable connector to fold upon itself in the nested position without protruding significantly from the earstem.

According to yet another aspect, the first and second optical elements 50, 70 can be used in combination to provide a dual element projection assembly, as illustrated in FIGS. 2 and 12A-C. In this regard, it is contemplated that any of the features and embodiments described herein can be incorporated into either a single or dual element projection assembly. As mentioned above, in the dual element project assembly embodiment, each of the first and second optical elements 50, 70 can be formed to include orientation indicators 190 in order to achieve symmetrical positioning of the first and second elements 50, 70. Thus, the first and second optical elements 50, 70 can be positioned such that the optical beams projected from the first and second transmission surfaces 56, 76 can be projected on to the retinas 126', 126" of the wearer within the respective ranges of allowability 118', 118".

According to another implementation, the first and second optical elements 50, 70 can be configured to be at least partially incorporated or nested into the frame 12 of the eyeglass 10. In some embodiments, the first and second optical elements 50, 70 can be nestable along the respective ones of the first and second orbitals 14, 16 of the frame 12. In this regard, the first and second optical elements 50, 70 can be formed to correspond to the general shape and curvature of the first and second orbitals 14, 16. It is contemplated that the first and second orbitals 14, 16 can be formed to provide a groove or slot into which the respective ones of the first and second optical elements 50, 70 can be positioned in a nested position. The first and second optical elements 50, 70 can be connected to the posterior portion 60 or the anterior portion 62 of the frame 12. By being connected to the frame 12, it is contemplated that the first and second optical elements 50, 70 can be deployed into the wearer's field of view, and despite the normal movement of the wearer, maintain a stable position.

Figure 12A:
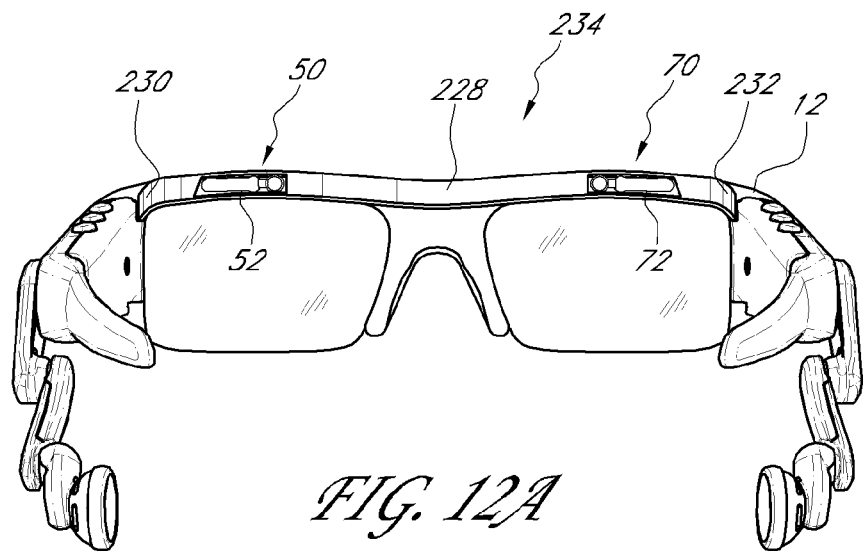
FIG. 12A is a rear view of another embodiment wherein the projection assembly is provided on a frame of the eyeglass and includes a swingbar which supports the first and second adjustable optical elements, wherein the swingbar is in a retracted position, in accordance with an embodiment.

Further, the projection assembly can be configured such that the first and second optical elements 50, 70 are coupled together for at least a portion of their adjustable movement. For example, FIG. 12A is a rear view of an eyeglass 10 wherein the first and second optical elements 50, 70 are attached to a swingbar 228. The swingbar 228 can be configured to move from a retracted position 234 when the projection assembly is not in use (illustrated in FIG. 12A), to a deployed position 236 (illustrated in FIGS. 12B-C) that orients the first and second optical elements 50, 70 to be within the range of allowability in the field of view of the user. Thus, the swingbar 228 can tend to ensure that the first and second optical elements 50, 70 move in unison for at least a portion of the adjustable movement (termed "rough adjustment"), thereby improving the symmetrical positioning of the first and second optical elements 50, 70 within the wearer's field of view.

As described further below, the use of the swingbar 228 can ensure that the "rough adjustment" of the projection assembly relative to the wearer's eyes maintains the symmetry of the first and second optical elements 50, 70. A "fine adjustment" can subsequently be performed by manipulation of the first and second optical elements 50, 70.

Figure 12B:
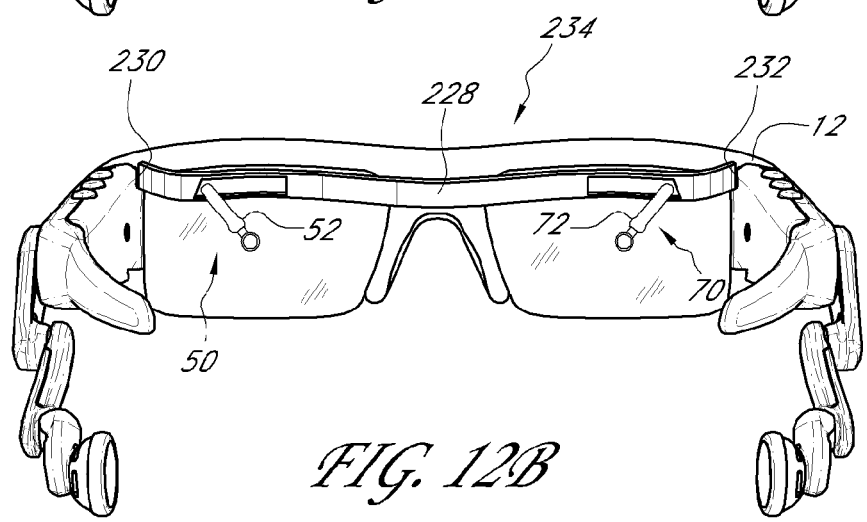
FIG. 12B is a rear view of the assembly of FIG. 12A, illustrating the swingbar in a deployed position.
Figure 12C:
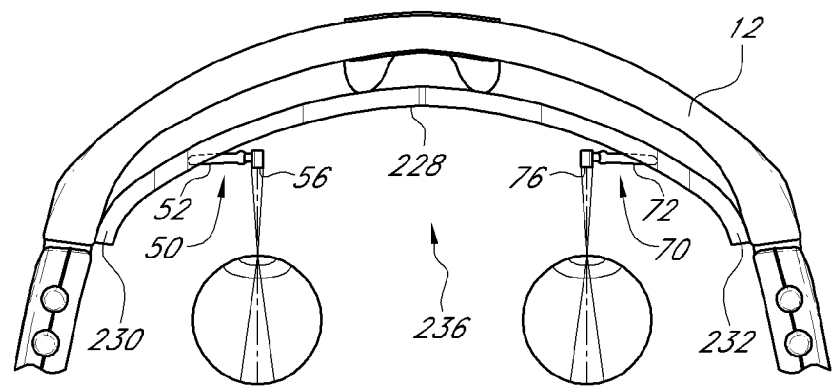
FIG. 12C is a top plan view of the assembly of FIG. 12B.

FIGS. 12A-C show an embodiment of the swingbar 228 wherein the swingbar 228 is elongate and includes a first end 230 and a second end 232. Although various operative connections and configurations can be utilized, the swingbar 228 can be an elongate bar that extends along at least a portion of the first and second orbitals 14, 16 of the frame 12. The swingbar 228 can extend along the entire length of the first and second orbitals 14, 16, as shown in FIGS. 12A-C, or only along a portion thereof, as desired.

The swingbar 228 can be formed to correspond to the general shape and curvature of the first and second orbitals 14, 16. Further, the first and second orbitals 14, 16 can be formed to provide a groove or slot into which the swingbar 228 can be positioned in a nested position. The swingbar 228 can be connected to the posterior portion 60 or the anterior portion 62 of the frame 12.

In some embodiments, the swingbar 228 can be pivotally mounted to the frame 12. In the embodiment illustrated in FIGS. 12A-C, the first end 230 and the second end 232 of the swingbar 228 can each be pivotally mounted to the posterior portion 60 of the frame 12. However, the swingbar 228 can also be centrally coupled to the frame 12 at a single pivot point, move by means of translation, or other forms of movement. In one implementation, the swingbar 228 can be configured to extend between centerpoints of the first and second orbitals 14, 16, and be pivotally coupled to the frame 12 at a point above the bridge 18.

As mentioned above, the swingbar 228 is preferably moveable from the retracted position 234 to the deployed position 236 so as to ensure that the first and second optical elements 50, 70 move symmetrically with the swingbar 228. Preferably, once the swingbar 228 is moved to the deployed position 236, thus providing the symmetrical "rough adjustment," the first and second optical elements 50, 70 can then be adjusted to provide the "fine adjustment" of the projection assembly.

As shown in the illustrative embodiment of FIG. 12B, the deployed position 236 of the swingbar 228 may only be slightly displaced from the retracted position 234 thereof. For example, the swingbar 228 may be operative to pivot within a range of approximately ⅛ to ½ inches, and preferably, approximately ¼ inch. In accordance with an embodiment, the swingbar 228 can be configured to be rigidly maintained in a position outside of the wearer's straight ahead line of sight, whether in the retracted position 234 or the deployed position 236. Thus, the projection assembly preferably does not obscure or block the wearer's view by placing bulky objects in the straight ahead line of sight, and such safety precautions should always be considered when using embodiments.

The swingbar 228 can be configured with the first and second optical elements 50, 70 being supported thereon. As illustrated in FIGS. 12A-C, the first and second optical elements 50, 70 can be mounted onto the swingbar 228 with the distal ends 82, 86 of the first and second adjustable connectors 52, 72 being pivotably connected thereto. A variety of configurations can be implemented. Preferably, the swingbar 228 can be configured such that the first and second optical elements 50, 70 can be nested against or in the swingbar 228 when the swingbar 228 is in the retracted position 234.

In another embodiment, when the swingbar 228 is in the deployed position 234, the first and second optical elements 50, 70 can be adjusted to enter the wearer's straight ahead line of sight and to project the optical beams onto the retinas, as described above. In the illustrated embodiment of FIG. 12B, when the swingbar 228 is moved to the deployed position 236, the first and second optical elements 50, 70 can be pivoted downwardly such that the optical beams projected from the first and second transmission surfaces 56, 76 can be projected onto the retinas 126', 126" of the wearer within the respective ranges of allowability 118', 118".

It is also contemplated that an implementation of the orientation indicator 190 can be incorporated into the eyeglass 10 shown in FIGS. 12A-C. Further, in order to ensure that the swingbar 228 journeys only intermediate the retracted position 234 to the deployed position 236, it is contemplated that a motion limiting element can also be included. For example, the motion limiting element can be: a protrusion that limits the pivotal motion of the swingbar 228; a rotation limiter that is disposed at the first and second ends 230, 232; a triangular recess along the posterior portion 60 of the frame 12 in which the swingbar 228 travels; and/or other structures. In this regard, the first end 230 and the second end 232 can be recessed into the frame or protrude therefrom. Various modifications can be implemented to ensure the accuracy and repeatability of the positioning of the swingbar 228.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. An optical display assembly configured to be attached to an eyewear comprising a frame, a lens, an orbital and a pair of earstems extending posteriorly relative to the frame, the optical display assembly comprising:

a support defining first and second ends, the first end of the support being attachable to a first lateral portion of an eyewear, the second end of the support being attached or attachable to a second lateral portion of the eyewear for maintaining the support in a stable position relative to the eyewear, the support being formed to correspond to a general shape and curvature of a portion of the eyewear; and an optical element configured to be supported by the optical display assembly, the optical element comprising a connector having first and second ends, the first end being configured to connect to and disconnect from a plurality of different structures of the optical display assembly, the second end being configured to support a transmission surface of the optical element, the connector being configured to articulate about a degree of freedom such that the transmission surface is adjustable relative to the first end of the connector, the transmission surface being configured to provide an optical display to the wearer.

2. The combination of the optical display assembly of claim 1 and an eyewear comprising a frame, a lens, an orbital and a pair of earstems extending posteriorly relative to the frame.

3. The optical display assembly of claim 2, wherein the support comprises an elongate body extending between the first and second lateral portions of the frame.

4. The optical display assembly of claim 2, wherein the connector is configured to connect to and disconnect from a portion of the frame.

5. The optical display assembly of claim 2, wherein the connector is configured to connect to and disconnect from portions of the earstems.

6. The optical display assembly of claim 2, wherein the connector is configured to connect to and disconnect from portions of the lens.

7. The optical display assembly of claim 1, wherein the degree of freedom corresponds to an x, y, or z axis.

8. The optical display assembly of claim 1, wherein the connector is configured to connect to and disconnect from the support.

9. An optical display assembly configured to be attached to an eyewear comprising a frame, a lens, an orbital and a pair of earstems extending posteriorly relative to the frame, the optical display assembly comprising:
- a support defining first and second ends, the first end of the support being attachable to a first portion of an eyewear, the second end of the support being attached or attachable to a second portion of the eyewear for maintaining the support in a stable position relative to the eyewear, wherein the first and second portions are spaced apart from each other, the support being formed to correspond to a general shape and curvature of a portion of the eyewear;
- an optical element configured to be supported by the eyewear, the optical element comprising a connector having first and second ends, the first end being configured to be removably attachable to a plurality of different structures of the optical display assembly, the second end being configured to support a transmission surface of the optical element, the second end being adjustable relative to the first end, the transmission surface being configured to provide an optical display to the wearer; and
- source electronics configured to be in electrical communication with the optical element, the source electronics comprising a sensor for determining positional location such that the source electronics is configured to provide a display of a map and an indicator of the positional location of a wearer on the map to the optical element.

10. The combination of the optical display assembly of claim 9 and an eyewear comprising a frame, a lens, an orbital and a pair of earstems extending posteriorly relative to the frame.

11. The optical display assembly of claim 10, wherein at least a portion of the frame is configured to allow wires for the source electronics to extend therebetween.

12. The optical display assembly of claim 10, wherein the connector is configured to connect to and disconnect from a portion of the frame.

13. The optical display assembly of claim 9, wherein the connector is configured to connect to and disconnect from the support.

14. A method of making an optical display assembly comprising:
- providing a support defining first and second ends, the first end of the support being attachable to a first lateral portion of an eyewear, the second end of the support being attached or attachable to a second lateral portion of the eyewear for maintaining the support in a stable position relative to the eyewear, the support being formed to correspond to a general shape and curvature of a portion of the eyewear; and
- providing an optical element configured to be supported by the optical display assembly, the optical element comprising a connector having first and second ends, the first end being configured to connect to and disconnect from a plurality of different structures of the optical display assembly, the second end being configured to support a transmission surface of the optical element, the connector being configured to articulate about a degree of freedom such that the transmission surface is adjustable relative to the first end of the connector, the transmission surface being configured to provide an optical display to the wearer.

15. The method of claim 14, further comprising attaching the optical display assembly to an eyewear comprising a frame, a lens, an orbital and a pair of earstems extending posteriorly relative to the frame.

16. The method of claim 14, further comprising connecting the connector to the support.

17. The method of claim 14, further comprising connecting the connector to the frame.

18. The method of claim 14, further comprising providing source electronics configured to be in electrical communication with the optical element and extending wires for the source electronics between at least a portion of the frame.

* * * * *

UNITED STATES PATENT AND TRADEMARK OFFICE
CERTIFICATE OF CORRECTION

PATENT NO. : 8,876,285 B2  Page 1 of 1
APPLICATION NO. : 14/046165
DATED : November 4, 2014
INVENTOR(S) : James H. Jannard It is certified that error appears in the above-identified patent and that said Letters Patent is hereby corrected as shown below:

In column 2 (page 6, item 56) at line 36, Under Other Publications, change "Infringment;" to --Infringement;--.

In column 2 (page 6, item 56) at line 42, Under Other Publications, change "Injuction;" to --Injunction;--.

In the Specification

In column 14 at line 26, Change "minor" to --mirror--.

Signed and Sealed this
Twenty-seventh Day of October, 2015

Michelle K. Lee
*Director of the United States Patent and Trademark Office*